United States Patent
Whisenant et al.

(10) Patent No.: US 8,221,405 B2
(45) Date of Patent: Jul. 17, 2012

(54) PATENT FORAMEN OVALE CLOSURE DEVICE AND METHODS FOR DETERMINING RF DOSE FOR PATENT FORAMEN OVALE CLOSURE

(75) Inventors: Brian K. Whisenant, Salt Lake City, UT (US); Clark C. Davis, Holladay, UT (US); Scott Miles, Sandy, UT (US); Richard Linder, Sandy, UT (US); Daryl Edmiston, Draper, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 1445 days.

(21) Appl. No.: 11/671,428

(22) Filed: Feb. 5, 2007

(65) Prior Publication Data

US 2008/0045937 A1    Feb. 21, 2008

Related U.S. Application Data

(60) Provisional application No. 60/771,004, filed on Feb. 6, 2006, provisional application No. 60/775,382, filed on Feb. 20, 2006.

(51) Int. Cl.
*A61B 18/18* (2006.01)
(52) U.S. Cl. ............... 606/33; 606/41; 606/232
(58) Field of Classification Search ............... 606/32–41
See application file for complete search history.

(56) References Cited

U.S. PATENT DOCUMENTS

| | | | |
|---|---|---|---|
| 4,957,656 A | 9/1990 | Cerny et al. | |
| 5,545,200 A | 8/1996 | West et al. | |
| 5,827,276 A | 10/1998 | LeVeen et al. | |
| 6,022,347 A | * | 2/2000 | Lindenmeier et al. ......... 606/38 |
| 6,050,992 A | 4/2000 | Nichols | |
| 6,063,082 A | 5/2000 | DeVore et al. | |
| 6,197,022 B1 | 3/2001 | Baker | |
| 6,258,087 B1 | 7/2001 | Edwards et al. | |

(Continued)

FOREIGN PATENT DOCUMENTS

WO    WO/99/18871    4/1999

OTHER PUBLICATIONS

International Search Report dated Oct. 25, 2007, for International Application No. PCT/US07/61713 (2 pages).

(Continued)

*Primary Examiner* — Linda Dvorak
*Assistant Examiner* — Amanda Scott
(74) *Attorney, Agent, or Firm* — Holland & Hart LLP

(57) ABSTRACT

A medical system and device for use in delivering RF energy to a tissue opening and a method for determining an RF dose is disclosed. In one embodiment, the medical device includes an electrode or anchor and one or more devices, such as an impedance electrode, RF electrode and/or thermocouple. The electrode or anchor can be deployed from a delivery shaft inside the left atrium, for example, of a heart and substantially conform to the tissue proximate the tissue opening. Tissue characteristics, such as temperature and/or impedance, can be measured, before, during and after application of RF energy to the tissue, by one or more devices to determine an RF dose. After energy is applied to the tissue between the left and right electrodes, the left electrode can be removed from the left atrium by being received back into the delivery shaft and the delivery shaft thereafter removed from the opening.

8 Claims, 18 Drawing Sheets

U.S. PATENT DOCUMENTS

| | | | |
|---|---|---|---|
| 6,312,429 B1 | 11/2001 | Burbank et al. | |
| 6,325,797 B1 | 12/2001 | Stewart et al. | |
| 6,463,332 B1 * | 10/2002 | Aldrich | 607/101 |
| 6,645,198 B1 | 11/2003 | Bommannan et al. | |
| 6,805,129 B1 | 10/2004 | Pless et al. | |
| 6,908,464 B2 | 6/2005 | Jenkins et al. | |
| 6,939,348 B2 | 9/2005 | Malecki et al. | |
| 6,944,490 B1 * | 9/2005 | Chow | 600/374 |
| 6,970,742 B2 | 11/2005 | Mann et al. | |
| 6,974,454 B2 | 12/2005 | Hooven | |
| 6,976,986 B2 | 12/2005 | Berube | |
| 7,165,552 B2 | 1/2007 | Deem et al. | |
| 7,186,251 B2 | 3/2007 | Malecki et al. | |
| 7,257,450 B2 | 8/2007 | Auth et al. | |
| 7,293,562 B2 | 11/2007 | Malecki et al. | |
| 7,367,975 B2 | 5/2008 | Malecki et al. | |
| 2002/0022864 A1 | 2/2002 | Mahvi et al. | |
| 2004/0158239 A1 | 8/2004 | Behl et al. | |
| 2004/0193147 A1 | 9/2004 | Malecki et al. | |
| 2004/0230185 A1 | 11/2004 | Malecki et al. | |
| 2004/0243122 A1 | 12/2004 | Auth et al. | |
| 2004/0260278 A1 | 12/2004 | Anderson et al. | |
| 2004/0267191 A1 | 12/2004 | Gifford et al. | |
| 2005/0021016 A1 | 1/2005 | Malecki et al. | |
| 2005/0033288 A1 | 2/2005 | Auth et al. | |
| 2005/0034735 A1 | 2/2005 | Deem et al. | |
| 2005/0080406 A1 | 4/2005 | Malecki et al. | |
| 2005/0119647 A1 * | 6/2005 | He et al. | 606/41 |
| 2005/0125032 A1 | 6/2005 | Whisenant et al. | |
| 2005/0131401 A1 | 6/2005 | Malecki et al. | |
| 2005/0131460 A1 | 6/2005 | Gifford et al. | |
| 2005/0192627 A1 | 9/2005 | Whisenant et al. | |
| 2005/0192654 A1 | 9/2005 | Chanduszko et al. | |
| 2006/0027241 A1 | 2/2006 | Malecki et al. | |
| 2006/0074410 A1 | 4/2006 | Malecki et al. | |
| 2006/0079870 A1 | 4/2006 | Barry | |
| 2006/0241581 A1 | 10/2006 | Malecki et al. | |
| 2006/0241582 A1 | 10/2006 | Malecki et al. | |
| 2006/0241583 A1 | 10/2006 | Malecki et al. | |
| 2006/0241584 A1 | 10/2006 | Malecki et al. | |
| 2006/0247612 A1 | 11/2006 | Malecki et al. | |
| 2006/0271030 A1 | 11/2006 | Francis et al. | |
| 2006/0271040 A1 | 11/2006 | Horne et al. | |
| 2006/0271089 A1 | 11/2006 | Alejandro et al. | |
| 2006/0276779 A1 | 12/2006 | Malecki et al. | |
| 2006/0276846 A1 | 12/2006 | Malecki et al. | |
| 2007/0010806 A1 | 1/2007 | Malecki et al. | |
| 2007/0044811 A1 | 3/2007 | Deem et al. | |
| 2007/0078485 A1 | 4/2007 | Deem et al. | |
| 2007/0088355 A9 | 4/2007 | Auth et al. | |
| 2007/0093804 A1 | 4/2007 | Kaveckis et al. | |
| 2007/0093805 A1 | 4/2007 | Auth et al. | |
| 2007/0100324 A1 | 5/2007 | Tempel et al. | |
| 2007/0106214 A1 | 5/2007 | Gray et al. | |
| 2007/0112347 A1 | 5/2007 | Malecki et al. | |
| 2007/0123824 A1 | 5/2007 | Kaveckis | |
| 2007/0123851 A1 | 5/2007 | Alejandro et al. | |
| 2007/0123852 A1 | 5/2007 | Deem et al. | |
| 2007/0123934 A1 | 5/2007 | Whisenant et al. | |
| 2007/0203479 A1 | 8/2007 | Auth et al. | |
| 2007/0287999 A1 | 12/2007 | Malecki et al. | |
| 2008/0009859 A1 | 1/2008 | Auth et al. | |
| 2008/0033421 A1 | 2/2008 | Davis et al. | |
| 2008/0033425 A1 | 2/2008 | Davis et al. | |
| 2008/0045937 A1 | 2/2008 | Whisenant et al. | |
| 2008/0215085 A1 | 9/2008 | Whisenant et al. | |

OTHER PUBLICATIONS

U.S. Appl. No. 60/803,479, filed May 30, 2006, titled, Methods, Systems, and Devices for Closing a Patent Foramen Ovale Using Mechanical Structures.

U.S. Appl. No. 60/809,566, filed May 31, 2006, titled, Methods, Systems, and Devices for Closing a Patent Foramen Ovale Using Mechanical Structures.

* cited by examiner

PATENT FORAMEN OVALE CLOSURE DEVICE AND METHODS FOR DETERMINING RF DOSE FOR PATENT FORAMEN OVALE CLOSURE

CROSS-REFERENCE TO RELATED APPLICATIONS

This application claims benefits from U.S. Provisional Patent Application Ser. No. 60/771,004 filed on Feb. 6, 2006, entitled "DEVICE AND METHODS FOR DETERMINING RF DOSE FOR PFO CLOSURE," and U.S. Provisional Patent Application Ser. No. 60/775,382 filed on Feb. 20, 2006, entitled "PATENT FORAMEN OVALE CLOSURE DEVICE USING RADIO FREQUENCY ENERGY," the contents of which are hereby incorporated by reference in their entirety.

BACKGROUND OF THE INVENTION

1. The Field of the Invention

The present invention relates generally to medical devices and methods of use for closing tissue openings such as patent foramen ovale ("PFO"). More particularly, the present invention relates to devices, systems, and methods for closing a PFO by applying radio frequency ("RF") energy to the tissue in and/or around the PFO and for determining an RF dosage to be applied to the tissue.

2. The Relevant Technology

Physical malformations or defects that are present at birth can be detrimental and even lethal when left uncorrected. A PFO is an example of a cardiac birth defect that can be problematic and even result in death when combined with other factors such as blood clots or other congenital heart defects. A PFO occurs when an opening between the upper two chambers of the heart fail to close during or after birth. This birth defect is sometimes also known as a "hole in the heart."

Some of the problems associated with a PFO can occur when a blood clot travels between the left and right atria of the heart through the PFO, and ends up on the arterial side. A blood clot in the left atrium can be passed through the aorta and travel to the brain or other organs, and cause embolization, stroke, or a heart attack. A PFO can be treated by being closed by a surgical procedure. Additionally, other similar defects (e.g., septal or otherwise) where some tissue needs to be closed in order to function properly can include the general categories of atrial-septal defects ("ASDs"), ventricular-septal defects ("VSCs") and patent ductus arterosus ("PDA"), and the like.

FIGS. 1A-1C depict various views of a heart having a PFO. The heart 10 is shown in a cross-section view in FIG. 1A. In a normal heart 10, the right atrium 30 receives systemic venous blood from the superior vena cava 15 and the inferior vena cava 25, and then delivers the blood via the tricuspid valve 35 to the right ventricle 60. However, in the depicted heart 10 a septal defect, which is shown as a PFO 50, is present between right atrium 30 and left atrium 40.

The PFO 50 is depicted as an open flap on the septum between the heart's right atrium 30 and left atrium 40. In a normal heart 10, the left atrium 40 receives oxygenated blood from the lungs 40 via pulmonary veins 75, and then delivers the blood to the left ventricle 80 via the bicuspid valve 45. In a heart 10 having a PFO 50 some systemic venous blood also passes from the right atrium 30 through the PFO 50 and mixes with the oxygenated blood in left atrium 40, and then is routed to the body from left ventricle 80 via aorta 85.

During fetal development of the heart 10, the interventricular septum 70 divides the right ventricle 60 and left ventricle 80. In contrast, the atrium is only partially partitioned into right and left chambers during normal fetal development, which results in a foramen ovale fluidly coupling the right and left atrial chambers. As shown in FIG. 1B, when the septum primum 52 incompletely fuses with the septum secundum 54 of the atrial wall, the result can be a tunnel 58 depicted as a PFO 50, or an ASD (not shown).

FIG. 1C provides a view of the crescent-shaped, overhanging configuration of the septum secundum 54 from within the right atrium 30 in a heart 10 having a PFO 50. The septum secundum 54 is defined by its inferior aspect 55, corresponding with the solid line in FIG. 1C, and its superior aspect 53 represented by the phantom line, which is its attachment location to the septum primum 52. The septum secundum 54 and septum primum 52 blend together at the ends of the septum secundum 54. The anterior end 56a and posterior end 56p are referred to herein as "merger points" for the septum secundum 54 and septum primum 52. The length of the overhang of the septum secundum 54, which is the distance between superior aspect 53 and inferior aspect 55, increases towards the center portion of the septum secundum as shown.

The tunnel 58 between the right atrium 30 and left atrium 40 is defined by portions of the septum primum 52 and septum secundum 54 between the merger points 56a and 56p which have failed to fuse. The tunnel 58 is often at the apex of the septum secundum 54 as shown. When viewed within right atrium 30, the portion of the septum secundum 54 to the left of tunnel 58, which is referred to herein as the posterior portion 57p of the septum secundum, is longer than the portion of the septum secundum 54 to the right of tunnel 58, which is referred to herein as the anterior portion 57a of the septum secundum. In addition to being typically longer, the posterior portion 57a also typically has a more gradual taper than the anterior portion 57a as shown. The anterior pocket 59a is the area defined by the overhang of the anterior portion 57a of the septum secundum 54 and the septum primum 52, and it extends from the anterior merger point 56a toward the tunnel 58. Similarly, the posterior pocket 59p is the area defined by the overhang of the posterior portion 57p of septum secundum 54 and the septum primum 52, and it extends from the posterior merger point 56p toward the tunnel 58.

Conventional treatments for PFO, and other related conditions have generally involved invasive surgery, which also presents a risks to a patient. Although there are some less invasive treatments for PFO, such treatments have been less efficient at closing the PFO opening than techniques involving invasive surgery. One current method of correcting a PFO involves the use of an electrode for delivering RF energy to the tissue surrounding the PFO. Applying RF energy to the area around the PFO can weld the tissue together and damage the tissue to initiate tissue growth that joins both sides of the PFO opening. Unfortunately, existing RF PFO closure devices have not been capable of satisfactory closure, resulting in additional medical procedures, some of which are more invasive than the initial attempt to close the PFO.

Therefore, it would be advantageous to have an improved device or system and method of use that can be used in order to deliver the RF dose and/or determine the RF dose needed for treating a PFO. Additionally, it would be advantageous for the device or system to be configured to utilize catheter technology and anchors in order to deliver the RF dose locally to the tissue surrounding the PFO.

BRIEF SUMMARY OF THE DISCLOSURE

The invention relates to a medical system, medical device and method for use in reducing the size of an internal tissue opening, such as a patent foramen ovale ("PFO"). In one embodiment, the system can include a medical device and one or more devices, such as a thermocouple, impedance electrode and/or RF electrode, for use in measuring a tissue characteristic which can be used to determine an RF dosage. The medical device can include a generally elongate member having at least one expandable portion. This at least one expandable portion can have one or more struts or legs that form an anchor or electrode usable to move at least one of the septum secundum and/or septum primum to reduce the size of the PFO. The anchor can be conductive, either directly or through the use of conductive structures mounted to the anchor, to enable RF energy to be applied to the tissue in and/or around the PFO.

The one or more devices can be coupled to the anchor, for example, to aid in measuring a tissue characteristic. For example, in one embodiment, the medical system includes a first and second impedance electrode positioned to be useable to measure the impedance of the tissue proximate the PFO. The impedance measurement can aid in determining the size of the PFO to in turn aid in determining an RF dose to treat the PFO. Similarly, the medical system can include a first and second thermocouple positioned to be usable to measure the temperature of the tissue proximate the PFO. Knowledge of the temperature and impedance characteristics of the tissue in and/or around the PFO can aid in determining an RF dose to treat the PFO.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE INVENTION

Figure 1A:
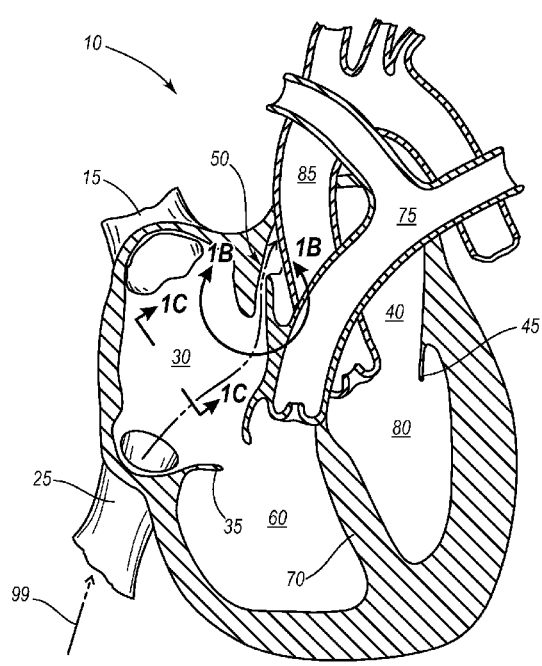
FIG. 1A is a cross-sectional view illustrating a heart.

The present invention extends to systems, methods, and apparatus for reducing the size of an internal tissue opening. By way of explanation, the devices disclosed herein can be used for a variety of internal tissue opening, although, for purposes of simplicity, frequent reference is made herein to reducing the size of or closing an opening in heart tissue known as patent foramen ovale ("PFO"). Accordingly, it will be understood that references to PFO openings are not limiting of the invention.

In the following description, numerous specific details are set forth to assist in providing an understanding of the present invention. In other instances, well-known aspects of PFO closure devices or medical devices in general have not been described in particular detail in order to avoid unnecessarily obscuring the present invention. In addition, it is understood that the drawings are diagrammatic and schematic representations of certain embodiments of the invention, and are not limiting of the present invention nor are they necessarily drawn to scale.

Illustrative embodiments of the invention relate to delivering radio frequency or RF energy to the septal wall of the heart to treat a defect known as a patent foramen ovale ("PFO"). In order to treat this type of defect it can be desirable to have an electrode system that can hold the walls of the flap-like defect together while energy is applied to "weld" the defect closed, i.e. damage the tissue to stimulate tissue growth in the area. Furthermore, it can be desirable to have a system that enables a practitioner to more effectively determine the amount of RF energy to apply, as well as the amount of time to apply such amount of RF energy.

In one embodiment, the medical device can include an electrode configured to increase the effectiveness of the tissue weld. The effectiveness of the tissue weld can be increased by configuring the electrode to contact, and in some instances conform with, the tissue of the atrium proximate the opening of the PFO. Furthermore, the electrode can be configured to be collapsible to a small cross section to remove the electrode from the welded tissue opening without substantially interfering the damaged tissue.

Furthermore, the present invention relates to medical devices, medical systems, and methods of use for delivering, measuring and/or determining the proper RF dosage applied to an electrode at a PFO for delivering RF energy to the tissue surrounding the PFO in order to induce closure of the PFO. The medical device can include a catheter that can be inserted into a vein and routed to the heart, and passed through the right atrium into the PFO. A portion of the medical device can also optionally pass into the left atrium. The catheter can be configured to deliver RF energy to the tissue surrounding the PFO, and measure and/or determine the RF dose for inducing the PFO to close. Optionally, the medical device and medical systems can be configured for measuring and/or determining the optimal RF dose to treat the PFO.

In one embodiment, the medical device and system can include one or more thermocouples and associated equipment for measuring temperature. The thermocouple can be placed in or proximate the PFO, which may include being within the right atrium, left atrium, and/or PFO tunnel as well as in contact with the respective walls thereof. The thermocouple can be fixed to the medical device in a variety of locations, referred to herein as measurement locations. For example, one or more measuring devices can be fixed to an electrode or arm of the medical device, or they can be housed in a lumen of a catheter thus enabling a practitioner to position the thermocouple independent from the electrode or arm, or a combination thereof as will be described more fully herein. The thermocouple can be configured to measure the temperature of the tissue at or around the PFO.

Knowledge of the temperature proximate the PFO can be advantageous because the temperature required to denature proteins in the tissue and weld tissues together and/or elicit a healing response that occludes the PFO is generally at least about 50 degrees C. As such, the thermocouple can provide an indication of the amount of RF energy that is needed to close and/or treat a PFO by measuring the temperature over a period of time. The thermocouple can be used to measure the temperature before and/or during treatment of the PFO with RF energy.

In one embodiment, the medical device and system can include at least one impedance electrode and associated hardware for measuring impedance. The impedance electrode can be delivered with a catheter so as to be proximate the tissue surrounding the PFO. As such, the impedance electrode can facilitate determination of the impedance or resistance of the tissue surrounding the PFO to be determined. A determination of the impedance or resistance of the tissue can be used to determine the amount and duration of RF energy to apply to the tissue to damage and thereby induce tissue regrowth to close the PFO.

Also, the impedance of the tissue can be correlated with the temperature of the tissue, wherein impedance decreases as the temperature increases. As such, when the tissue is heated by RF energy, its electrical impedance decreases. This gives the possibility of using impedance measurements to determine the state of heating of the atrial tissue. Accordingly, during a PFO closure procedure that uses RF energy, the impedance and/or resistance of the surrounding tissue can change. This allows for a change in impedance to provide an indication of the amount of RF dose needed to induce the PFO to close. Thus, the impedance electrode(s) can be useful in determining the dose of RF energy needed to induce closure of the PFO.

The initial impedance of the heart tissue, such as a septum tissue, can be measured and correlated to body temperature. Also, the initial impedance measurement can be used to gain information about the thickness of the tissue, length of the PFO tunnel, and/or the like. This information can be used to determine the initial RF power setting or power increase(s)/decrease(s) that may be used to achieve a given tissue heating rate. The tissue thickness information may also be used in the determination of the amount of dwell time at a target temperature that may be used for the heat to adequately diffuse into the tissue to induce injury and subsequent tissue regrowth. Tissue thickness may also be estimated from x-ray images illustrating the distance between proximal and distal anchors, or from marks on the proximal ends of operable cathters.

Also, the initial impedance of the heart tissue can be processed through an appropriate algorithm in order to predict an amount of RF energy or RF dose needed to induce closure of a PFO. As such, the various types of information regarding the PFO that can be ascertained by impedance and temperature measurements can be applied to an algorithm to estimate a minimum through maximum level of RF energy that may be needed and/or the minimum through maximum dwell time or duration that may be needed at any particular RF energy level, impedance level, and/or tissue temperature. In any event, the tissue of a PFO can be characterized by the initial impedance and/or temperature measurement and compared against standardized parameters so that the thickness of the tissue, length of the PFO, and/or the like can provide an estimate of the RF dose that may be required to induce closure.

Additionally, the impedance and/or temperature of the tissue can be measured and monitored during an RF dosing procedure. During the RF dosing procedure the change in tissue impedance can be used to determine an appropriate RF dose for treating the internal tissue opening. This can include using the change in impedance and/or temperature to calculate changes in tissue thickness and the like. Also, the change in impedance and/or temperature can be used to determine whether or not the PFO is sufficiently injured to induce closure, close, or reduce in size such that the treatment is useful. Furthermore, the change in impedance can be used to calculate the approximate temperature of the tissue based on impedance-temperature correlations or characteristics.

Moreover, the RF dose estimation can be used in conjunction with real-time impedance measurements and/or impedance changes that occur during a PFO dosing procedure. As such, an RF dose estimation based on the initial impedance values that have been processed through an algorithm can be used as a standard for comparing with the actual impedance values so that real-time changes in the RF dose can be made to account for actual changes in tissue impedance. This can be implemented with computer or human controlled changed that modulate the RF energy or dwell time at selected RF energies, impedance levels, and/or temperatures to provide improved RF dosing measurements.

Optionally, the medical device and system can measure the tissue resistance similar to the measure of inductance. The embodiments of the medical device and system described here can be modified to measure changes in the resistance of tissues, such as the heart tissue or septum tissue. Such modifications from measuring tissue impedance to tissue resistance are well within the capabilities of one of ordinary skill in the art in view of the disclosure provided herein.

It will be appreciated by one of ordinary skill in the art in view of the disclosure provided herein that the medical device and system can include one or more thermocouples, a combination of at least one thermocouple and at least one impedance electrode pair, and/or at least one impedance electrode pair to facilitate measuring and/or determining an RF dose for closing and/or treating a PFO or other internal tissue opening.

A plurality of measuring devices can be utilized to generate a representative characteristic profile of the tissue, such as multiple thermocouple sensors to generate a temperature profile. For example, in one embodiment multiple thermocouple sensors are located proximate the tissue of each of the left atrium, PFO tunnel, and right atrium to generate a temperature profile and/or to facilitate the determination of an appropriate RF dose. Moreover, impedance measurements alone or the combination with temperature measurements can provide additional information about the tissue. For example, impedance and/or temperature measurements can provide information about the temperature at different locations, such as at the surface or inside of the atrial tissue, changes in such temperatures, thickness of the tissue, changes in thickness, appropriate RF dose to induce closure of the PFO, and the like.

As will be appreciated by one of ordinary skill in the art in view of the disclosure provided herein, the present invention can be used in connection with various closure devices and components used to treat and/or close a PFO or other internal tissue opening. For example, right atrial anchors, such as those with two, three, or more fingers or arms can be used to help reduce the size of the PFO. Also, the right and/or left atrial anchors alone or in combination can be used to deliver RF energy to the tissue of the PFO, or can be used as an implant that is implanted at the PFO to facilitate closure after RF energy has been applied.

Examples of right and/or left atrial anchors which can utilize the invention disclosed herein are described in U.S. patent application Ser. No. 10/964,311, entitled "PATENT FORAMEN OVALE (PFO) CLOSURE DEVICES, DELIVERY APPARATUS AND RELATED METHODS AND SYSTEMS," filed Oct. 12, 2004, and U.S. patent application Ser. No. 11/102,095, entitled "PATENT FORAMEN OVALE CLOSURE DEVICES, DELIVERY APPARATUS AND RELATED METHODS AND SYSTEMS," filed Apr. 8, 2005, the contents of which are hereby incorporated by reference in their entirety.

I. PFO Closure Device

Generally, the present invention includes a closure device, such as a PFO closure device 100. Details regarding PFO closure devices, delivery devices and related methods are disclosed in U.S. patent application Ser. No. 11/534,996, entitled "DELIVERY SYSTEM FOR PATENT FORAMEN OVALE CLOSURE DEVICE," filed Sep. 25, 2006, and U.S. patent application Ser. No. 11/534,953, entitled "COMPLIANT ELECTRODE FOR PATENT FORAMEN OVAL CLOSURE DEVICE," filed Sep. 25, 2006, the contents of which are hereby incorporated by reference in their entirety.

Figure 2:
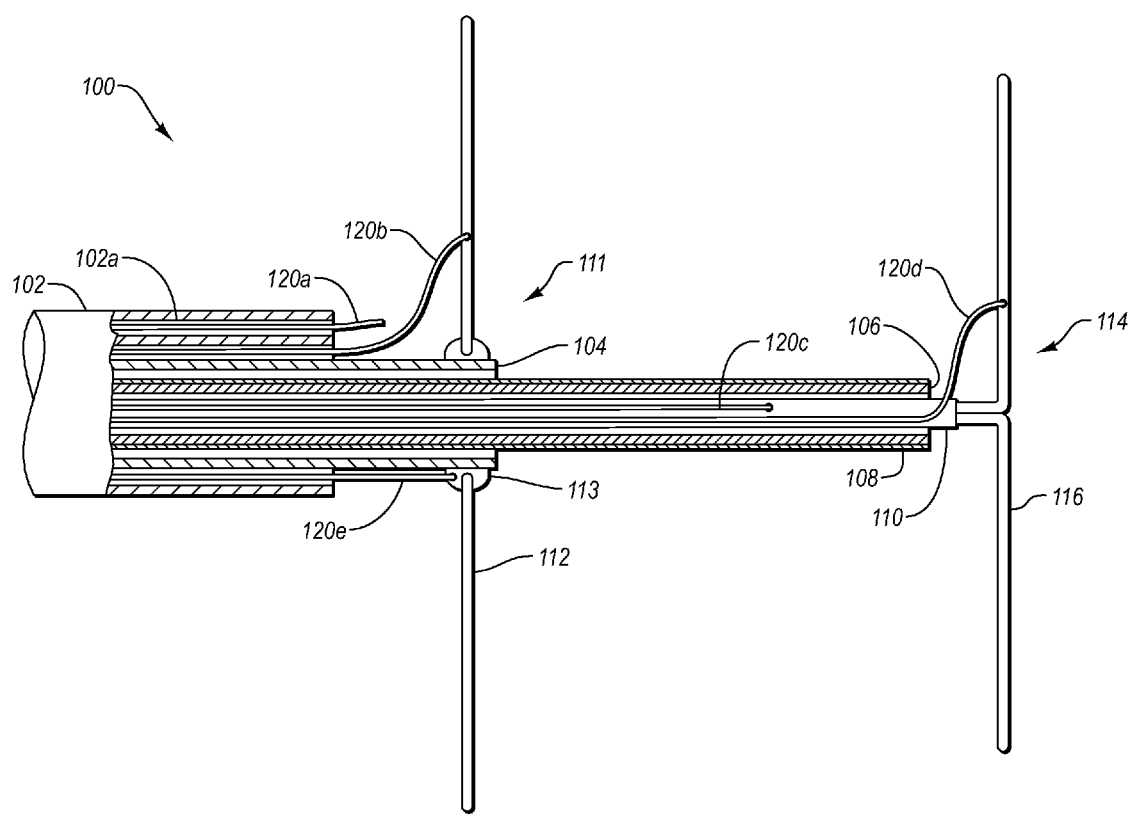
FIG. 2 is a cross-sectional view illustrating a medical device.

FIG. 2 illustrates an embodiment of a PFO closure device 100. In the illustrated embodiment, closure device 100 can include a left electrode 114, a right electrode 111 and a delivery sheath 102 configured to facilitate positioning of left and right electrodes 114, 111. Elements associated with left electrode 114 can include one or more arms 116, a delivery shaft 110 that can be configured to house at least a portion of arms 116, a left electrode delivery tube 106 that can be configured to receive delivery shaft 110 therein, wherein delivery shaft 110 can translate and/or rotate therein, and insulation 108 on the outer surface of left electrode delivery tube 106.

Elements associated with right electrode 111 can include one or more arms 112 coupled to a right electrode catheter 104 by one or more hubs 113. In the illustrated embodiment, arms 112 are coupled to right electrode catheter 104 by hubs 113. Furthermore, right electrode catheter 104 can receive left electrode delivery tube 106 therein such that left electrode delivery tube 106 can translate and/or rotate in right electrode catheter 104.

Furthermore, closure device 100 can include one or more devices 120 for use in reducing the size of an internal tissue opening. Device 120 can be an RF electrode, an impedance electrode, or a temperature measuring devices such as a thermocouple, or a combination thereof. For example, in one embodiment, devices designated as 120a and 120c can be thermocouples usable to determine temperatures and devices designated as 120b, 120d and 120e can be impedance electrodes.

Additionally, the delivery sheath 102 can be configured to include thermocouples and associated hardware and wiring for measuring the temperature at the PFO or of the tissue surrounding the PFO. This can include a left thermocouple that is disposed at least proximate with the left electrode 114, such as device 120d, a tunnel thermocouple that is disposed at, on or in delivery shaft 110, such as device 120c, and/or a right thermocouple that is disposed at least proximate right electrode 111, such as devices 120a, 120b or 120e. This allows for measuring the temperature of the tissue surrounding the PFO at the left atrium wall (e.g., left side of septum), within the PFO tunnel (e.g., between the septum secundum and septum primum), and at the right atrium wall (e.g., right side of septum).

Furthermore, delivery sheath 102 can be configured to include impedance electrodes and associated hardware and wiring for measuring the impedance across the atrial wall separating the right atrium from the left atrium, or through the PFO tunnel. This can include delivery sheath 102 having at least one left impedance electrode, for example that is disposed at least proximate with a left closure device, at least one tunnel impedance electrode that is disposed at least proximate with a tunnel closure device, and/or at least one right impedance electrode that is disposed at least proximate with a right closure device. This allows for measuring the impedance of the tissue surrounding the PFO at the left atrium wall (e.g., left side of septum), within the tunnel (e.g., between the septum secundum and septum primum), and at the right atrium wall (e.g., right side of septum).

As discussed previously, devices 120 can be positioned in a variety of locations in order to achieve a certain result. For example, device 120a can be positioned in a separate lumen 102a of delivery sheath 102 so as to allow a practitioner to independently move device 120a with respect to delivery sheath 102 and/or right electrode 111, if desired. This can be advantageous, in that it can allow a practitioner to handle a proximal portion of device 120a and move device 120a in a proximal or distal direction while maintaining the position of delivery sheath 102 and/or right electrode 111. As also shown in the illustrated embodiment, the distal end of device 120b can be coupled to arm 112 of right electrode 111, device 120d can be coupled to arm 116 of left electrode 114, and device 120e can be coupled to hub 113. In this manner, devices 120b, 120d and 120e may be in a position to more accurately measure the temperature, impedance or resistance of the skin adjacent the electrodes. Furthermore, device 120c can be coupled to delivery shaft 110 such that device 120c can measure various characteristics inside the PFO tunnel 99 when delivery shaft 110 is positioned therein. It will be understood that devices 120 can be coupled to closure device 100 in a variety of ways. For example, the distal end of device 120 can be fixed to closure device 100 by an adhesive. Alternatively, device 120 can be received through an aperture in closure device 100 to secure device 120 to closure device 100.

As will be appreciated by one of ordinary skill in the art in view of the disclosure provided herein, closure device 100 can include multiple devices 120 positioned in a variety of locations to facilitate measurement of one or more characteristics such as temperature, impedance or resistance, and/or to deliver RF energy. Furthermore, devices 120 can include insulation as needed in order to allow the device to function as intended.

Furthermore, in connection with devices 120, the PFO closure device 100 can include arms 114, 112 having one or more of the following functionalities: (a) arms configured as an RF electrode; (b) arms configured as an atrial anchor; (c) arms configured as a thermocouple; (d) arms configured to include shape memory materials; (e) arms configured as impedance electrodes; and (f) combinations thereof.

Closure device 100 can be used for transcatheter closing of a tissue opening, such as a PFO. The elements of closure device 100 pertaining to left electrode (116, 110, 106, and 108) can be configured to be inserted through a hole which can occlude as tissue growth occurs due to the delivery of RF energy. The approach for transcatheter treatment of a PFO can be through the femoral vein and the inferior venacava into the right atrium of the heart. As such, it can be advantageous for the electrode and/or associated elements to have a low crossing profile. A low crossing profile can enable the internal tissue opening to be reduced in size and still allow the electrode and/or associated elements to be withdraw after the energy delivery and/or "tissue welding" have been accomplished.

Additionally, the left electrode can be configured as a left anchor that is implanted at the left atrial wall.

Figure 3:
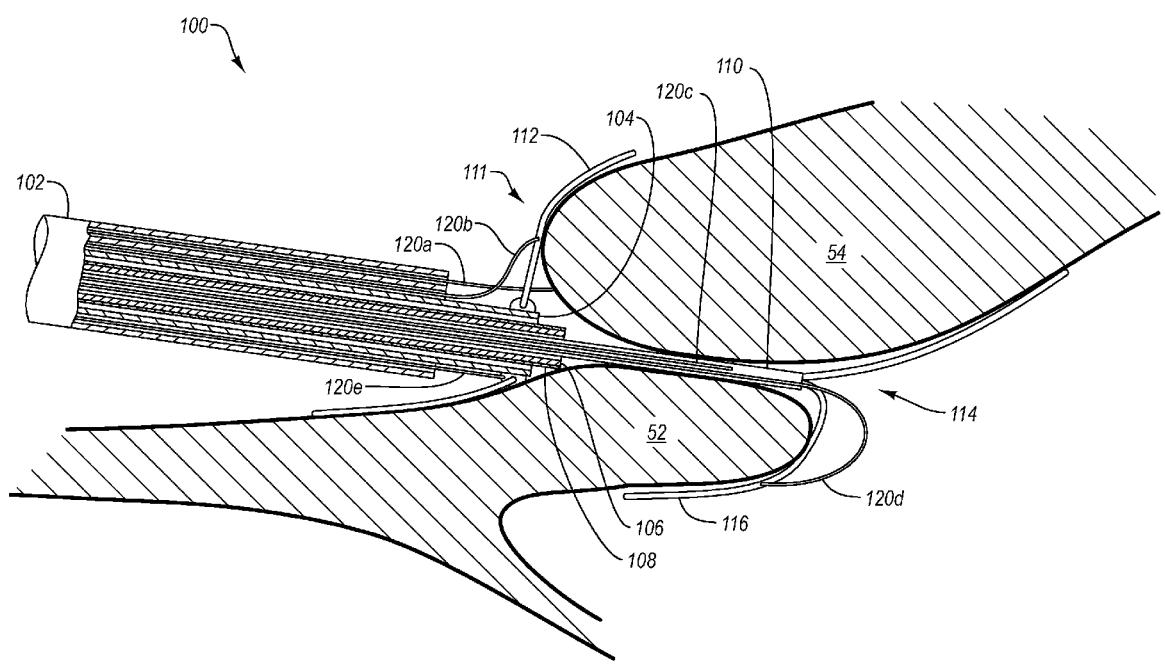
FIG. 3 is a cross-sectional view illustrating the medical device of FIG. 2 positioned within a heart.

FIG. 3 illustrates the positioning of an electrode through a PFO into the left atrium of a heart. As shown in the illustrated embodiment, various elements associated with left electrode 114 can be inserted through the opening of the PFO. For example, delivery shaft 110 and left electrode delivery tube 106 which can enclose at least a portion of left anchor delivery shaft 110, can be received within the tunnel of the PFO. An approach for transcatheter treatment of a PFO is through the femoral vein and the inferior venacava into the right atrium of the heart. As such, it can be advantageous for the member or electrode that passes through the PFO into the left atrium to have a low crossing profile. A low crossing profile can enable the member or electrode to be withdraw through a smaller hole after the energy delivery and/or "tissue welding" have been accomplished.

In the illustration, delivery sheath 102 can be outside a right electrode catheter 104. When right electrode catheter 104 is extended from delivery sheath 102, right electrode 111 can be deployed such that arms 112 can extend. When right electrode catheter 104 is withdrawn into delivery sheath 102, arms 112 can collapse and enter the right electrode catheter 104.

Left electrode delivery tube 106 can be inside the right electrode catheter 104 and can have insulation 108 in its exterior surface to electrically insulate between the right electrode catheter 104 and the conductive left electrode delivery tube 106 and the conductive delivery shaft 110. Alternatively, insulation can be positioned on the interior surface of left electrode delivery tube 106 or can be positioned on the exterior surface of delivery shaft 110. Furthermore, insulation can be positioned on the interior and exterior surface of left electrode delivery tube 106 and the exterior surface of delivery shaft 110, or any combination thereof.

Delivery shaft 110 can have various shapes, but can be tubular at the distal opening so that left electrode 114 opens radially when deployed. When left electrode 114 is extended from delivery shaft 110, the arms 116 of left electrode 114 can assume their trained or predetermined orientation when arms comprise a shape memory material. When left electrode 114 is withdrawn into delivery shaft 110, arms 116 return to a straightened orientation. In this manner, left electrode 114 can have an increased surface area outside delivery shaft 110 than would otherwise be possible to insert in a patient. In other words, left electrode 114 can be pushed out of and pulled back into a tube with a diameter of about 1 mm, for example, and yet expand to a diameter of about 20 mm, for example, and have enough strength to hold the atrial walls together during energy delivery and strongly resist pulling through the PFO.

In the illustrated embodiment, devices 120 are coupled to closure device 100 in various locations. For example, device 120b is coupled to arm 112, device 120c is coupled to delivery shaft 110, device 120d is coupled to arm 116, and device 120e is coupled to hub 113. Furthermore, in the illustrated embodiment, device 120a is extended to contact the skin adjacent the PFO. In this manner, devices 120 can be utilized to measure various characteristics relevant for making a determination of proper RF dosage. For example, in one embodiment, devices 120b and 120d are impedance electrodes and devices 120a, 120c and 120e are thermocouples. Impedance measurements can be taken utilizing devices 120b and 120d and septal tissue temperature can be measured utilizing devices 120a, 120c and 120e. The measurements from devices in connection with the knowledge of the approximate locations of these devices can facilitate a determination of the size of the PFO and an appropriate RF dose to facilitate closure of the PFO.

Once an RF dosage is determined and with arms 112 of right electrode 111 and arms 116 of left electrode 114 being positioned as illustrated, energy can be applied to the tissue which is between arms 112 and arms 116. The application of energy in this manner can cause tissue damage. Causing tissue damage in this manner can initiate tissue regrowth so as to weld the tissue together. Utilizing devices 120, measurements can be taken during the application of RF energy to the tissue, or alternatively can deliver additional RF energy when devices are RF electrodes. Taking measurements during the application of RF energy can enable the determination of modifications to the amount and/or duration of RF energy being applied to the tissue. After such treatment, delivery shaft 110 can be advanced back through the small remaining hole in the PFO and left electrode 114 can be pulled into delivery shaft 110 and left anchor delivery shaft 110 withdrawn without substantially disturbing the weak "tissue weld" that has been created by the procedure.

Electrodes 111 and 114 discussed herein can include specific details similar to the electrodes as disclosed and designated as 100, 311 and 314 in U.S. patent application Ser. No. 11/534,953, entitled "COMPLIANT ELECTRODE FOR PATENT FORAMEN OVAL CLOSURE DEVICE", filed Sep. 25, 2006.

Figure 4:
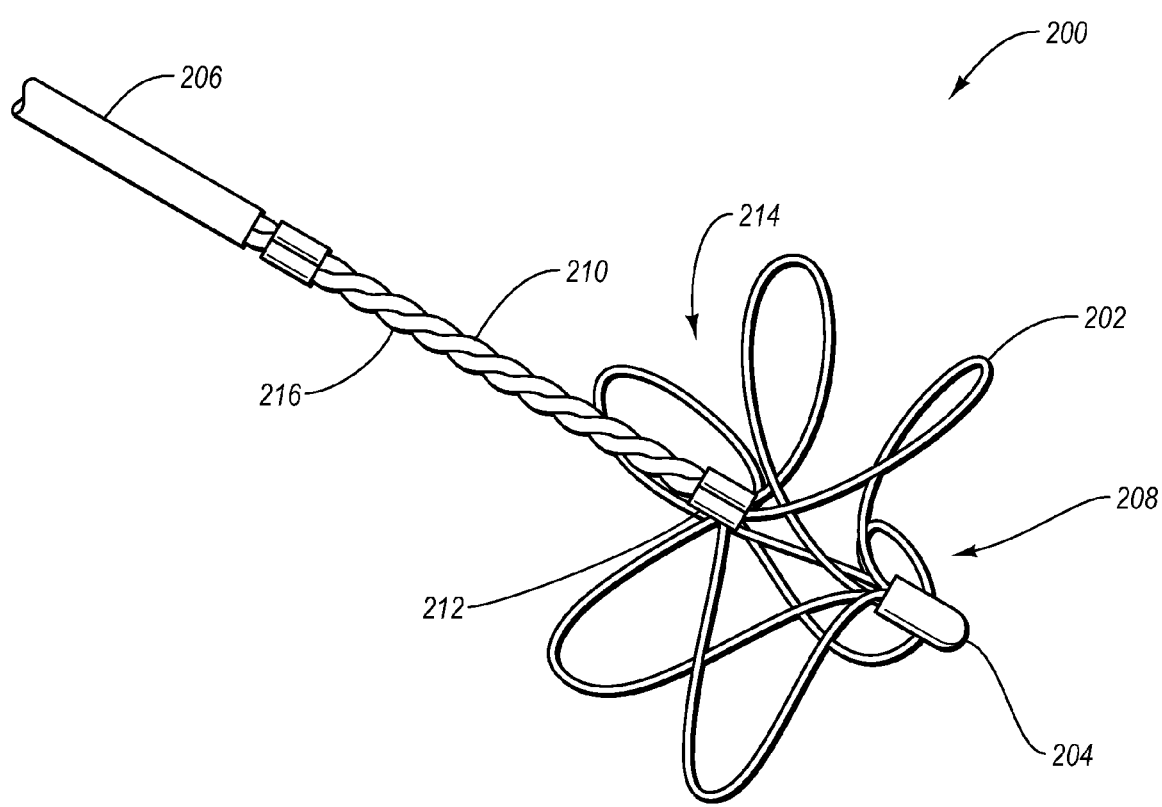
FIG. 4 is a perspective view illustrating an embodiment of an electrode or anchor.

FIG. 4 is a perspective view of an alternative embodiment of a left electrode 200. In the illustrated embodiment, electrode 200 can include arms 202, which can open to form a generally spherical shape, although other shapes that range from spherical through planar can also be achieved. Arms 202 can be deployed from a catheter 204 or optionally a delivery tube 206 similar to delivery tube 106 as depicted in FIGS. 2 and 3, through actuation of a delivery shaft 210. The arms 202 are shown in a deployed position, wherein they extend radially out from delivery shaft 210. Arms 202 can be configured to be coupled at their distal ends 208.

In one embodiment, each arm 202 can be coupled together with an end clamp 204 so that each arm is coupled with the other arms at the distal ends 208. Optionally, a proximal clamp 212 can be used to couple the proximal ends 214 of the arms 202 together. The combined use of end clamp 204 and proximal clamp 212 can increase the stability and functionality of electrode 200. Also, end clamp 204 and/or proximal clamp 212 can be comprised of a radiopaque material to aid with positioning electrode 200 within the left atrium, right atrium and/or PFO tunnel. In any event, the shape formed by multiple arms 202 can be configured and shaped so as to optionally lock together as the arms become coplanar in order to increase the nonlinear deflection characteristic of the arms by using one or more clamps.

It will be understood by one of ordinary skill in the art in view of the disclosure provided herein that one or more devices, such as thermocouples, RF electrodes and impedance electrodes can be utilized in connection with electrode 200 as described above.

Electrode 200 can be configured as other closure devices in that it can be pushed out of and pulled back into a delivery tube with a diameter of about 1 mm (e.g., about 0.25 mm to about 2.5 mm) and yet expand to a diameter of about 20 mm (e.g., about 10 mm to about 40 mm). Also, the joined arms 202 of electrode 200 can be configured to substantially hold the atrial walls together during RF energy delivery and resist pulling through the PFO when electrode 200 is left electrode, and resist being pushed through the PFO when electrode 200 is a right electrode.

In one embodiment, arms 202 can be crimped together at three locations (although crimping at lesser or greater than three locations is possible). Such crimping can be mechanical or through a clamp, clasp, or the like. In any event, arms 202 can be joined at their distal ends 208, at their proximal ends 214, and a distance, approximately 3 cm for example, away from the proximal ends 214. The portion between the most proximal crimp and the crimp at the proximal ends 214 can form a flexible portion 216. Flexible portion 216 can be configured to provide some flexibility to electrode 200. Flexibility of electrode 200 due to flexible portion 216 can enable electrode 200 to more easily conform to the surface against which it is to be positioned. Optionally, arms 202 can be twisted to form a helix in the flexible portion 216 as illustrated. As will be appreciated by one of ordinary skill in the art in view of the disclosure provided herein, the flexible portion 216 can be of varied size and length in order to achieve a desired degree of flexibility.

As will be understood by one of ordinary skill in the art in view of the disclosure provided herein, electrode 200 can function as an anchor, RF electrode, thermocouple, impedance electrode, and/or the like. Furthermore, clamps 204 and 212 can be configured as an RF electrode, thermocouple, impedance electrode, and/or the like.

It will be understood by one of ordinary skill in the art in view of the disclosure provided herein that an electrode can be configured to operate in a mono-polar format. In this manner, the electrode can be energized in the mono-polar mode to heat the tissue adjacent the electrode to induce closure of tissue opening, such as a PFO.

The position of an electrode with respect to the septum secundum 54 and septum primum 52 can be similar to the position described in the related U.S. patent applications having Ser. No. 10/964,311, entitled "PATENT FORAMEN OVALE (PFO) CLOSURE DEVICES, DELIVERY APPARATUS AND RELATED METHODS AND SYSTEMS," filed Oct. 12, 2004, Ser. No. 11/102,095, entitled "PATENT FORAMEN OVALE CLOSURE DEVICES, DELIVERY APPARATUS AND RELATED METHODS AND SYSTEMS," filed Apr. 8, 2005, Ser. No. 11/534,996, entitled "DELIVERY SYSTEM FOR PATENT FORAMEN OVALE CLOSURE DEVICE," filed Sep. 25, 2006, and Ser. No. 11/534,953, entitled "COMPLIANT ELECTRODE FOR PATENT FORAMEN OVAL CLOSURE DEVICE," filed Sep. 25, 2006.

It will be understood in view of the disclosure herein that elements which can serve as an RF electrode can operate in a mono-, bi- or multi-polar mode to achieve a desired result.

The foregoing closure devices, electrodes and arms can have various configurations. For example, the arms can include a hollow core or lumen that can be used for an RF electrode, thermocouple, and/or impedance electrode, to electronically communicate with a controller or associated equipment for delivering RF energy or measuring a characteristic. Also, the arms can include a core having an electronically conductive material that is surrounded by a shape memory material that is further surrounded by a radiopaque material. For example, an arm can include a solid nitinol wire core with a platinum alloy coil wrapped over the nitinol to provide radiopacity. Another example can include a nitinol tube with a stranded platinum wire inside the lumen of the tube to achieve radiopacity. A further example can include a nitinol tube having a electronically conductive copper alloy wire inside the lumen of the tube and an outer wrapping made of a platinum alloy coil.

The closure device and electrode disclosed herein can have any number of arms. The closure device and/or electrode can be configured with a suitable number of arms so that a proper amount of closure device or electrode can be applied over an appropriate area. This can include modulating the number of arms so that the arm density is increased or decreased depending on the needs of the application, such as RF dosing, temperature sensing, and/or impedance measuring.

In one embodiment, the closure device or electrode, such as electrode 200, can include arms that have been given a shape memory such that the arms form pre-defined shapes after being deployed from the lumen of the delivery shaft. As such, this can include each arm crossing over other arms or the central axis to form intersections when pulled into a substantially planar configuration. Also, the closure device can be comprised of a single arm that is configured to have a memory shape that forms any of the shapes depicted and/or described herein. In part, this is because of the shape memory materials enable a single arm or multiple arms to form an array of patterns for use as a closure device, which can further be useful as anchors, RF electrodes, thermocouples, and/or impedance electrodes.

It will be understood by one of ordinary skill in the art in view of the disclosure provided herein that arms of an electrode or closure device can be shaped to form a variety of patterns once deployed. Examples of patterns include spheres, spheroids, cubes, cylinders, cubes, triangles, other polygons, complex shapes, portions thereof, and combinations thereof.

In one embodiment, the closure device can be a left RF electrode. In the instance the closure device is a left RF electrode it is configured to be inserted through the PFO tunnel by catheter insertion. That is, the left RF electrode is inserted through the PFO tunnel and into the left atrium by use of the delivery shaft. Once within the left atrium, the left RF electrode can be expanded out of the delivery shaft. The left electrode can then be pulled against the left atrial wall tissue, such as the septum tissue, and compacted to a substantially planar configuration. The left RF electrode can then be retracted into the delivery shaft after sufficient RF energy has been delivered.

In one embodiment, the closure device can be a right RF electrode. In the instance the RF electrode is configured as a right RF electrode it can be delivered into the right atrium where it is expanded. However, the right RF electrode can be pushed against the right atrial wall for delivery of RF energy. The right RF electrode can thereafter be retracted into the delivery shaft.

In one embodiment, the closure device can be a right-to-left RF electrode. A right-to-left RF electrode is configured to include both aspects of a right RF electrode coupled with a left RF electrode. As such, each side can be expanded independently or simultaneously. This can include the right and left portions being coupled through the PFO tunnel or being mutually exclusive. A sliding mechanism can be used to compact the right and left portions against their respective sides of the atrial wall. Alternatively, a single RF electrode can be configured to extend through the PFO tunnel and contact the atrial tissue on each side by use of the shape memory materials. In addition to a PFO tunnel, other body lumens may also be closed by this device, for example atrial appendages.

In one embodiment, the closure device can be a PFO tunnel RF electrode. Also, the medical device can employ a single RF electrode that is configured to be inserted within the PFO tunnel and expand into the memory shape within the PFO tunnel. This allows for RF energy to be delivered directly into the tissue that defines the PFO tunnel.

Similarly, the closure device can be an RF electrode configured to induce tissue regrowth adjacent an internal tissue opening. While an embodiment of the invention has been described in connection with a PFO, the invention can be modified for treatment in connection with a variety of internal tissue openings. As such, the dimensions of the closure device, electrodes and arms can be modified for particular uses. Also, the amount of RF dose can be modulated depending on the thickness of the tissue and length of the hole. As discussed previously, the thickness of the tissue can be approximated by measuring the impedance of the skin utilizing devices 120.

In one embodiment, the closure device can be a left anchor. As such, the left closure device can be configured into a left anchor for contacting and anchoring into the atrial tissue. The left anchor can be beneficial for holding the closure device against the tissue. Left anchors are well known in art can be configured into removable anchors or implantable anchors.

Similarly, closure device can be a right anchor. This can include the arms forming a right anchor with or without being configured to deliver RF energy. Also, the right anchor can be used along with the left anchor in order to secure the PFO tissue. Right anchors are well known in the art and can be configured to be removable anchors or implantable anchors.

In one embodiment, the closure device can be a right-to-left anchor. This can include the aspects of the right and left anchors described above. As such, the anchor can anchor the right side of the PFO with the left side with a single configuration. This can be illustrated by combining a right anchor with a left anchor as separate aspects or a unitary piece.

It will be understood by one of ordinary skill in the art in view of the disclosure provided herein that devices 120 can be utilized in connection with anchors of a PFO closure device, such as those disclosed in U.S. patent applications having Ser. No. 10/964,311, entitled "PATENT FORAMEN OVALE (PFO) CLOSURE DEVICES, DELIVERY APPARATUS AND RELATED METHODS AND SYSTEMS," filed Oct. 12, 2004, and Ser. No. 11/102,095, entitled "PATENT FORAMEN OVALE CLOSURE DEVICES, DELIVERY APPARATUS AND RELATED METHODS AND SYSTEMS," filed Apr. 8, 2005.

In one embodiment, the closure device can be a PFO tunnel anchor with or without sharp points to impinge into the PFO tunnel tissue. Optionally, arms 112 and 116 depicted in FIGS. 2 and 3 can be configured to include a sharp tip on at least one of the arms. Also, it may be preferable for the tunnel anchor comprised of the arms to take a substantially cylindrical shape that may or may not include baskets or cubes on either end. In any event, the arms of the tunnel anchor may or may not include sharp tips which can penetrate into the atrial tissue. Sharp tips that penetrate into the atrial tissue can be beneficial for anchoring and delivering the RF energy directly into the tissue. Similarly, the RF electrode can be any hole anchor with or without arms having sharpened tips.

In one embodiment, the closure device can be configured as a right atrium closure device, which can be referred to generally as an implantable right closure device for simplicity. Such an implantable right closure device can be configured to be implantable at the tissue of the right atrium surrounding the PFO. Also, the implantable right closure device can be used in cooperation with an implantable left atrium closure device. Alternatively, an implantable left closure device can be implanted at the tissue of the left atrium surrounding the PFO, which can be implanted in conjunction with or without an implantable right closure device.

Moreover, the closure device can be configured as an implantable right-to-left atrial closure device, which can be placed at the right atrial tissue and extend through the PFO to also be placed at the left atrial tissue. Furthermore, the closure device can be configured as an implantable PFO tunnel closure device that is implanted substantially within the PFO tunnel. Additional information regarding implantable closure devices can be found in the incorporated references; whereby such references can be supplemented with the embodiments of the present invention described herein and modifications combining such references with the instant disclosure can provide closure devices with enhanced features.

Moreover, the embodiments of the closure device can be configured to include any combination of the foregoing functions in order to operate as an anchor, RF electrode, thermocouple, impedance electrode, or combination thereof.

II. Closure Device Arms

The present invention can be utilized in connection with a variety of PFO closure devices and delivery systems. For example, closure devices can include arms that are made of a shape memory material ("SMM"). For example, the SMM can be shaped in a manner that allows for restriction to induce a substantially linear orientation while within a delivery shaft, but can automatically retain the memory shape once extended from the delivery shaft. SMMs have a shape memory effect in which they can be made to remember a particular shape. Once a shape has been remembered, the SMM may be bent out of shape or deformed and then returned to its original shape by unloading from strain or heating. Some SMMs are super-elastic. This super-elastic characteristic allows large elastic strains to be imparted to the material prior to plastic deformation. This characteristic can aid in allowing the device to transition from the aforementioned substantially linear orientation to its retained memory shape. Typically, SMMs can be shape memory alloys ("SMA") comprised of metal alloys, or shape memory plastics ("SMP") comprised of polymers.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released the SMA can be capable of returning to the memory shape.

The are different types of SMAs. For example, SMAs can comprise: (a) copper-zinc-aluminium; (b) copper-aluminium-nickel, and (c) nickel-titanium ("NiTi") alloys known as nitinol. The NiTi alloys can be more expensive, but can have superior mechanical characteristics in comparison with the copper-based SMAs. The temperatures at which the SMA changes its crystallographic structure are characteristic of the alloy, and can be tuned by varying the elemental ratios.

For example, at least one of the arms can be comprised of a nickel-titanium allow that forms superelastic nitinol, which is a SMA. In the present case, nitinol materials can be trained to remember a certain shape, straightened in a shaft, catheter or other tube, and then released from the catheter or tube to return to its trained shape.

A SMP is a shape-shifting plastic that can be fashioned into arms that contain an electrically conductive metal. As such, the electrically conducting metal can be encapsulated within the SMP and have selected portions exposed therefrom in order to deliver the RF energy to the tissue surrounding the PFO. When an SMP encounters a temperature above the lowest melting point of the individual polymers, the blend makes a transition to a rubbery state. The elastic modulus can change more than two orders of magnitude across the transition temperature ("Ttr"). As such, an SMP can formed into a desired shape by heating it above the Ttr, fixing the SMP into the new shape, and cooling the material below Ttr. The SMP can then be arranged into a temporary shape by force, and then resume the memory shape once the force has been applied.

The SMPs shape-shifting plastic provides for implants, such as atrial anchors, to be placed in the heart via catheter technology and then expand into the memory shape when pushed through the delivery opening of the catheter. The SMPs can be configured to include conduits for containing electronically conductive materials for use in RF electrodes, thermocouples, and/or impedance electrodes. Also, the SMPs can include radiopaque materials for enhanced visualization by radiograph techniques.

In one embodiment, the SMP can be configured as an anchor that is implanted at the PFO. This is because the SMP can be comprised of a biodegradable polymer, which means they breakdown after a certain time period of being inserted into the body, such as in the heart. This can eliminate the need to remove the anchor. A biodegradable implant can also be comprised of a polymer which does not have shape memory properties. A biodegradable SMP can be comprised of at least two components with different thermal characteristics, such as oligo(ε-caprolactone)diol and crystallisable oligo(p-dioxanone)diol. The biodegradable SMP features two block-building segments characterized as a hard segment and a switching segment, which are linked together in linear chains. The higher-temperature shape is the plastic's memory form, which it assumes after heating. The SMP can be stretched or scrunched into temporary forms up to four times larger or smaller than its permanent memory shape, and retain the permanent memory shape when subjected to the appropriate stimuli, such as temperature.

Additionally, SMP can be comprised of polymers that are not biodegradable such as polynorborene, polyisoprene, styrene butadiene, polyurethane-based materials, vinyl acetate-polyester-based compounds, and others yet to be determined. As such, Many SMP can be used in accordance with the present invention.

For example, Veriflex™ shape memory polymer resin systems currently functions on thermal activation which can be customizable from −20° F. to 520° F., which allows for customization within the normal body temperature. This allows an arm that comprises Veriflex™ to be inserted into the PFO via a catheter, at which point it can be extended from the lumen of the delivery shaft. Once unrestrained by the delivery shaft, the body temperature can cause the arms to spontaneously take the shape of an atrial anchor. Also, this allows for various other shapes to be utilized as anchors as is well known in the art or later developed.

In one embodiment, an arm comprised of a SMM may be wrapped, coated, or filled with a radiopaque material such as platinum, barium sulphate or the like, to enhance the visibility of the device under fluoroscopy. Optionally, the radiopaque material is biocompatible. This can allow for the arm to be accurately placed within the heart proximate with the PFO. By way of example only, a PFO closure device can include seven arms each having an outer diameter of about 0.008 inches (e.g., 203 microns). Such arms can be comprised of the SMA NiTi, which are wrapped with a platinum ribbon having a thickness of 0.001 inches (e.g., 25.4 microns) and width of 0.003 inches (e.g., 76.2 microns). The NiTi arm wrapped with a platinum ribbon can be delivered through a tube with a bore of about 0.037" (e.g., 939 microns).

In one embodiment, the arm can be comprised of a SMM that retains the memory shape by temperature and a radiopaque material. The benefit of temperature-responsive memory shaping can be used to identify when an appropriate temperature has been obtained. For example, 50 degrees C. has been described as a suitable temperature for burning the tissue surrounding a PFO. When the arm resumes the memory shape at this temperature the formation of the anchor can be an indication that the suitable temperature has been achieved. Also, the radiopaque material can allow the change in shape to be monitored for association with temperature. This can be beneficial for left anchors, right anchors, PFO tunnel anchors, right-to-left anchors and the electrodes disclosed herein.

It will be understood by one of ordinary skill in the art in view of the disclosure provided herein that the foregoing details and features relating to arms can apply to closure device 100 and electrode 200. Furthermore, in one embodiment, an arm can be configured to include a blunt end. A blunt end on the tip of an arm can be used to reduce the possibility of an arm perforating the heart in instances such perforation is unfavorable. Examples of blunt ends can include the end of an arm having a non-sharp shape exemplified by a ball, cube, spheroid, and the like.

Figure 5A:
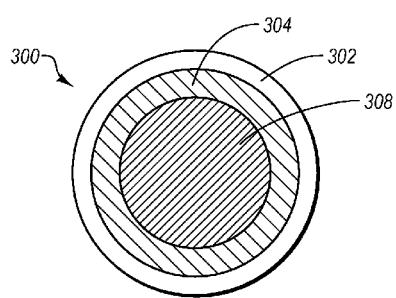
FIG. 5A is a cross-sectional view illustrating an embodiment of an arm of an electrode or anchor.
Figure 5B:
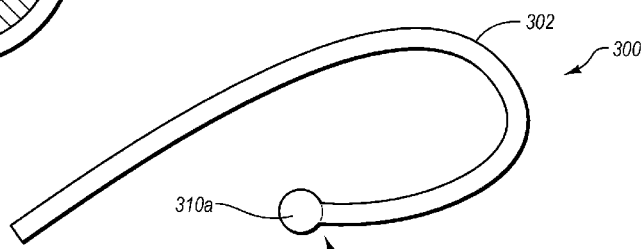
FIG. 5B is a perspective view illustrating an embodiment of an arm of an electrode or anchor.
Figure 5C:
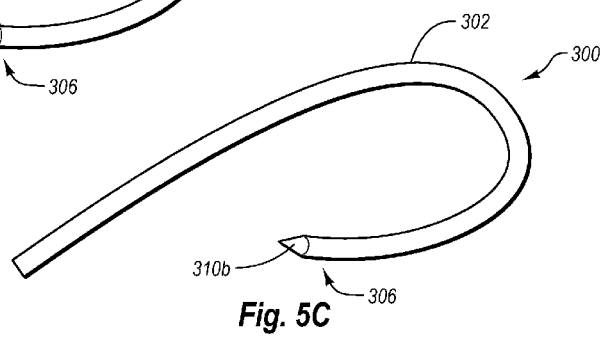
FIG. 5C is a perspective view illustrating an embodiment of an arm of an electrode or anchor.

FIGS. 5A-5C illustrate embodiments of an arm 300 in accordance with the present invention, which can be incorporated in closure device 100 and/or electrode 200. FIG. 5A is a cross-sectional view of a schematic diagram of an arm 300. In the illustrated embodiment, arm 300 includes more than one layer. Use of more than one layer can enable arm 300 to be multifunctional. For example, arm 300 can include an outer layer 302 comprised of a radiopaque material that completely or incompletely contains a middle layer 304. The middle layer 304 can be comprised of an SMM material to provide enhanced functionality of a terminating end or tip 306 of arm 300 toward the tissue of the PFO or atrial wall. Arm 300 can also include a central member or core 308 that is comprised of an electronically conductive material. As such, core 308 can be configured as an impedance electrode conduit, thermocouple conduit, or RF electrode conduit. Alternatively, the different layers can be switched in orientation and/or function.

Core 308 can be in electrical communication with a tip member 310 (e.g., depicted in FIG. 10B or 10C) and a controller or associated measurement equipment (not shown). Tip member 310 can be an impedance electrode, a thermocouple, or an RF electrode. As illustrated in FIG. 5B, tip member 310*a* is shown to be rounded which may be advantageous when it is desirable for the tip 306 to be blunt. On the other hand, FIG. 5C shows tip member 310*b* to be sharp which can be advantageous for penetrating the tissue in order to precisely measure impedance or temperature as well as for delivering RF energy.

Optionally, core 308 can be comprised of a conductive material to provide electronic coupling that also is compatible with or has SMM features, which can advantageously include a copper-based SMA. The impedance electrode conduit, thermocouple conduit, or RF electrode conduit can provide electronic communication between the medical device and/or system with an impedance electrode, thermocouple, or RF electrode, respectively.

Figure 6A:
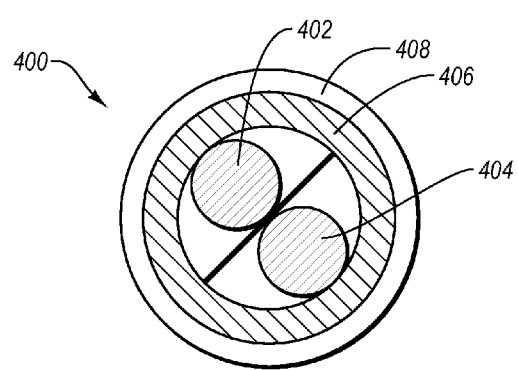
FIG. 6A is a cross-sectional view illustrating an embodiment of an arm of an electrode or anchor.
Figure 6B:
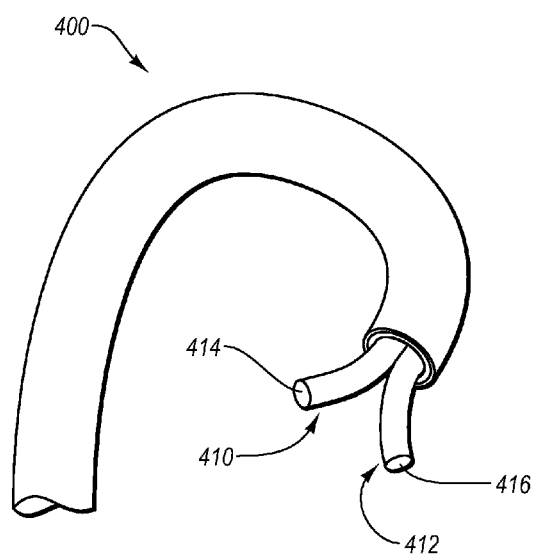
FIG. 6B is a perspective view illustrating an embodiment of an arm of an electrode or anchor.

FIGS. 6A and 6B provide illustrations of an embodiment of an arm 400 that includes two central members 402, 404. Similar to arm 300 as described with reference to FIGS. 5A-5C, central members 402, 404 can be electrically conducting conduits for electronic communications with tips 410 and 412. Central members 410, 412 can be any of a thermocouple conduit, RF conduit, and impedance conduit. Central members 410, 412 can be electronically coupled with a corresponding tip member 414, 416, and also electronically coupled with a medical device, medical system, controller, or associated measuring equipment. Accordingly, tip members 414, 416 can be any of a thermocouple, RF electrode, impedance electrode, and/or combination thereof. Moreover, central members 402, 404 can be enclosed by an intermediate layer 406, such as a SMM, and optionally an outer layer 408, such as a radiopaque covering.

Figure 7A:
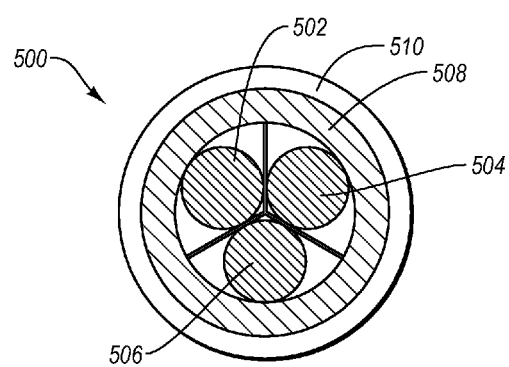
FIG. 7A is a cross-sectional view illustrating an embodiment of an arm of an electrode or anchor.
Figure 7B:
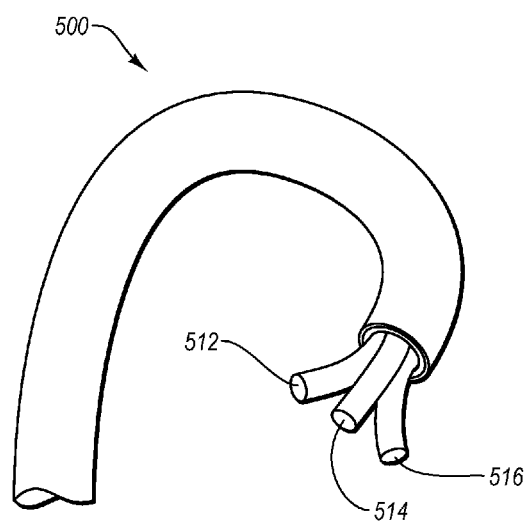
FIG. 7B is a perspective view illustrating an embodiment of an arm of an electrode or anchor.

FIGS. 7A-7B provide illustrations of an embodiment of an arm 500 that includes three central members 502, 504, and 506. Similar to arm 300 and arm 400, central members 502, 504, and 506 can be electrically conducting conduits for electronic communications with tips 512, 514, and 516, and also electronically coupled with a medical device, medical system, or controller. In one embodiment, central member 502 is a thermocouple conduit that electronically couples a thermocouple tip 512 with the medical device, medical system or associated measuring equipment; central member 504 is an impedance conduit that electronically couples an impedance electrode tip 514 with the medical device, medical system, or controller; central member 506 is an RF conduit that electronically couples an RF electrode tip 516 with the medical device, medical system, or controller. Moreover, central members 502, 504, and 506 can be at least partially enclosed by an intermediate layer 508, such as SMM, and optionally an outer layer 510, such as a radiopaque covering.

Embodiments of a closure device can have a range of arms, for example from 3 to 10 arms, made of superelastic NiTi, such as nitinol. In the present case, nitinol materials can be trained to remember a certain shape, straightened in a shaft, catheter or other tube, and then released from the catheter or tube to return to its trained shape. The arms may be wrapped, coated, or filled with a biocompatible radiopaque material such as platinum to enhance the visibility of the device under fluoroscopy. The ends of the arms may have a ball formed at the tip to reduce the possibility of an arm perforating the heart, or can be sharp to penetrate into the tissue.

By way of example, in one embodiment a closure device or electrode includes 7 arms having an average diameter of about 0.008 inches. The arms can include a hollow or solid tubular NiTi with an external wrapping comprised of a platinum ribbon with a 0.001 inch width and a 0.003 thickness. The closure device or electrode can be delivered through a tube with a bore of about 0.037 inches, which is slightly less than 1 mm.

It will be understood by one of ordinary skill in the art in view of the disclosure provided herein that details relating to arms as described with respect to FIGS. 5A-5C, 6A-6B and 7A-7B can be implemented with respect to other arms described herein, for example arms 112, 116, arms 202 to the extent applicable, and arms described in the U.S. patent applications disclosed herein. While various embodiments of arms have been depicted and described in connection with the figures, it should be recognized that the elements of such arms can be combined and/or modified within the scope of the invention. Also, various combinations of arms may be used in a closure device or electrode.

III. Thermocouple

As discussed herein above, the closure devices, electrodes and arms disclosed herein can be configured to act as a temperature measuring device, such as a thermocouple. The thermocouple can be configured as any temperature measuring device that is well known in the art or later developed. Also, the thermocouple can be of any functional size and in any functional shape. The purpose of the thermocouple is to enable the temperature of the atrial tissue, such as at the septum, to be measured before any RF energy is delivered, during the delivery of RF energy, and/or post delivery. Alternatively, the thermocouple can be usable to measure the temperature of the fluid passing through or proximate the PFO or surrounding tissue in order to provide Man indication of the temperature of the tissue. The thermocouple can enable the proper dose of the RF energy to be measured and/or determined, especially when multiple thermocouples are used and/or when used in conjunction with impedance electrodes. Thus, an accurate RF dose can be provided to close and/or treat a PFO.

Accordingly, as discussed previously, the thermocouple can be disposed at a variety of locations with respect to the arms, delivery shaft or closure device in general, as described herein and illustrated in the Figures. This can include the thermocouple being disposed at a tip of an arm or at any position along the arm. The arm can include a thermocouple lumen for a thermocouple conduit to extend therethough in order for a medical device or medical system to electronically communicate with the thermocouple.

In one embodiment, the thermocouple can be disposed in or adjacent a delivery shaft, thus causing the thermocouple to be positioned centrally with respect to the arms coupled to the delivery shaft. The central location can be beneficial for measuring the temperature that results from the delivery of RF energy. Furthermore, the central location can also be beneficial for determining temperatures in the PFO tunnel.

Alternatively, the thermocouple can be positioned within a thermocouple delivery sheath that is located within the closure device delivery sheath or in a central or secondary lumen of the closure device delivery sheath. This allows for the thermocouple to be extended from the delivery sheath as needed. Also, it may be advantageous in some instances for the centrally located thermocouple to have SMM materials so that it can be positioned on or proximate with an atrial tissue around the PFO.

It will be understood by one of ordinary skill in the art in view of the disclosure provided herein that other types of temperature measuring devices can be utilized without departing from the scope and spirit of the invention. For example, resistive temperature devices such as Resistance Temperature Detectors (RTD's) and thermistors can be utilized to facilitate the determination of temperatures in connection with the closure devices, electrodes and arms disclosed herein.

IV. Impedance Electrode

As discussed herein above, the closure devices, electrodes and arms disclosed herein can be configured to act as an impedance electrode. The impedance electrode can be configured as any impedance measuring device that is well known in the art or later developed. Also, the impedance electrode can be of any functional size and in any functional shape. The purpose of the impedance electrode is to enable the physical changes, such as temperature, thickness, impedance, and/or the like, in the atrial tissue, such as at the septum, to be measured before any RF energy is delivered, during the delivery of RF energy, and/or post RF delivery. The impedance electrode can enable the proper dose of the RF energy to be measured and/or determined, especially when multiple impedance electrodes are used and/or when used in conjunction with a thermocouple. Thus, an accurate RF dose can be provided to close and/or treat a PFO.

Accordingly, an embodiment of the present invention can utilize impedance technology in order to determine the amount and/or duration of RF energy that can be applied to a tissue, such as atrial tissue, for treating a PFO. The impedance of the tissue can be determined so that changes in impedance can be correlated to the amount of damage induced due to the RF energy. The impedance of tissue typically decreases as the temperature of the tissue increases, which allows for the impedance value to be correlated with a preferable temperature damaging the skin to treat a PFO.

In one embodiment, the impedance electrode can be configured to be incorporated into an arm as described herein. This allows an arm with or without SMM characteristics to deliver the impedance electrode to the tissue of the atrium or proximate therewith. An impedance electrode positioned in the vicinity of an atrial tissue can be used to measure the impedance by another electrode of an electrode pair being place on the opposite side of the PFO or external to the patient.

For example, the present invention can utilize an impedance electrode of an electrode pair being placed proximate with the PFO and the corresponding electrode being placed either on an external aspect of the patient, such as the skin, or proximate with atrial tissue on the opposite side of the PFO. Either placement of the electrodes can be beneficial for calculating the impedance value attributed to the tissue surrounding the PFO.

In another embodiment, the PFO closure device can include at least one right impedance electrode and at least one left impedance electrode. This can allow for the impedance value of the atrial tissue of the septum separating the right atrium from the left atrium to be calculated. Also, since the distance the electrical current needs to travel for an impedance measurement is small, such impedance values can be determined using lower power. The placement of the right and left impedance electrodes can be at the end of an arm, along any position of an arm, at the central axis of the delivery shaft, and/or extended from a delivery sheath to contact tissue. In any event, the placement of the impedance electrodes in the right and left aspects of the PFO closure device can be configured for calculating parameters of the atrial tissue that are beneficial for determining the RF dose required for closing and/or treating a PFO.

In one embodiment, all electrodes can be positioned external to the patient similar to that of impedance cardiography. Impedance cardiography includes well known techniques that utilize impedance of the thorax to determine the functionality of the heart. While impedance values are often used to calculate heart volume output, such output volumes can be inversely removed from cardiographic calculations so that the impedance value of the heart tissue can be isolated. Similarly, techniques and algorithms similar to impedance cardiography can be used to isolate the impedance value of the heart tissue during an RF dosing procedure. Changes in impedance value can provide an indication of the amount of PFO closure, atrial tissue damage, atrial tissue temperature, and similar parameters indicative of treating and/or closing a PFO. Thus, well known impedance cardiographic techniques can be modified for calculating the change in the impedance value of the heart tissue.

V. Methods of Using Impedance Measurements

As described above, the present invention can use electrical impedance measurements in conjunction with or without temperature measurements to determine RF dose, which includes RF energy and dwell time. As such, impedance measurements can enable prediction and real-time determinations of RF doses to be applied to the septal wall of the heart to treat PFO by inducing PFO closure. In order to treat this type of defect it can be desirable to have an impedance electrode system that predicts and/or determines the amount of RF energy to be applied to at least one wall surrounding a PFO. Furthermore, it can be desirable to have an impedance electrode system which facilitates holding the walls of the flap-like defect together while energy is applied to "weld" the defect by damaging the tissue to stimulate tissue growth in the area.

The process of measuring the impedance of the atrial tissue, such as the septum, can include a frequency range that is less than or equal to about 1 kHz in connection with the bioelectric component of tissue impedance. However, larger frequencies can be used. Similar to the process of determining impedance plethysmography, the frequency dependence of tissue impedance can be utilized as a factor for increasing the selectivity of measurement of the atrial tissue impedance. In part, this is because the impedance of different portions of tissues that have different reactive components or different thicknesses can be utilized and measured with currents applied at different frequencies. Thus, atrial preferential frequencies may be obtained.

Additionally, appropriate filtering of the impedance measurement may be done simultaneously with different frequencies in order to save measurement time and identify the impedance across different sections of heat tissue. Thus, selection of the atrial tissue impedance can be obtained at various points around a PFO. Such atrial impedances and associated changes due to RF energy can be tracked before, during, or after an RF dosing procedure for closing and/or treating a PFO. Also, the impedance values for different sections of tissue can be modeled and mapped using a computer and well known topographical programs that operate with impedance calculations and measurements For example, the impedance measurement can be made by introducing an electric current in the frequency range of about 20 to about 10000 kHz, and measuring the corresponding voltage. The ratio of voltage to current can provide an impedance Z. In order to eliminate the effect of the electrodes, separate electrode pairs for introducing the current and for measuring the voltage can be used. This can include an electrode pair that is used for introducing the current, and an electrode pair for measuring the voltage. However, a variety of electrode pair positioning may be chosen for current and/or for voltage measuring.

Generally, impedance measurements can use a single electrode pair, or utilize an electrode configuration similar to impedance cardiography, which utilizes four band electrodes. The physical arrangement of a pair of electrodes can include one electrode being placed at the atrial tissue around the PFO and the other on the opposite side of the tissue. Another electrode pair can include one electrode being placed at the tissue around the PFO, and the other on the external skin of the patient, such as at the chest or lower part of the neck.

The ability to utilize impedance measurements of the atrial tissue, such as the septum, can be attributed to the electrical properties of myocardial tissue, which are anisotropic due to the complex structure of the myocardial fiber orientation and the distribution of gap junctions therein. In part, this allows the measured myocardial impedance to differ depending on the current distribution and direction with respect to myocardial fiber orientation and, consequently, according to the measurement method. Accordingly, more then one method of impedance measurement can be used.

One method can include transmural measurements using an intracavitary catheter having an impedance electrode(s), and the other method consisted of nontransmural measurements using a four-needle probe inserted into the epicardium. Either method can provide an impedance value of the atrial tissue.

It will be understood by one of ordinary skill in the art in view of the disclosure provided herein that the methods of using impedance measurements can be incorporated into the various features of the closure devices, electrodes and devices disclosed herein.

Additional embodiments of the present invention relate generally to medical devices and methods of use for closing tissue openings such as a PFO. More particularly, exemplary embodiments of the present invention relates to devices, systems, and methods for closing a PFO by applying radio frequency ("RF") energy to the tissue in and/or around the PFO.

The present invention further extends to various concepts and variations of design, configuration and implementation of devices to be used for closing PFO'S. The medical device in accordance with one embodiment of the present invention can be generally simple to manufacture, easy for a surgeon to use, operable with minimal steps, can be reliable during operation and use, and can minimize the diameter needed to allow function and access while allowing withdrawal through a relatively small opening.

One embodiment of the present invention generally includes a medical device that can be positioned in close proximity to a PFO, used to position the septum secundum and/or septum primum to close the PFO, and then optionally apply RF energy to the tissue in and/or around the PFO. The medical device can be positioned using an actuator, slid within a catheter or along a guide wire, or function as a guide wire and be directed to the PFO without the aid of a catheter or guide wire extending substantially all the way to the heart.

The medical device can include a generally elongate member having at least one expandable portion. This at least one expandable portion can have one or more struts or legs that form an anchor usable to move at least one of the septum secundum and/or septum primum to close the PFO. The anchor can be conductive, either directly or through the use of conductive structures mounted to the anchor, to enable the RF energy to be applied to the tissue in and/or around the PFO. Furthermore, the medical device can include other devices, such as devices 120 described with respect to FIGS. 2 and 3, associated with one or more anchors and elements of the medical device.

The following discussion will be directed to various configurations of the medical device according to one embodiment of the present invention, but it will be understood that the medical device is only illustrative of one embodiment and does not limit the applicability of the general disclosure of the invention to other configurations and embodiments of medical devices that are capable of closing an opening within the heart or other body lumen of a patient. Further, although not illustrated, it will be understood that any of the described medical devices can include an integral soft tip, such as an atraumatic tip, J-hook, etc to aid with guiding the medical device. In addition, any of the described medical devices can cooperate with a separate guide wire that aids with navigating and positioning the medical device into the appropriate location, if desirable.

To aid with ease of explanation of the described medical device, the following terms will be identified and defined herein.

As used herein, the term "PFO" can refer to a Patent Foramen Ovale, Atrial Septal Defect (ASD), or other anatomic opening.

As used herein, the term "anchor" refers to an element of a PFO closure device between which the PFO or other anatomic structure is captured or located. These anchors can also serve as electrodes for sensing tissue characteristics and/or delivering energy to the PFO and/or tissue surrounding the PFO. The "anchor" can be made from one or more materials and have various configurations. For instance, the anchor can have all or portions thereof fabricated from one or more metals, alloys, polymers, plastics, synthetic materials, shape memory materials, including shape memory alloys and/or shape memory plastics, combinations thereof, or the like. More specifically, the "anchor" can be fabricated from stainless steel, other metals, plastics, elastomers, combinations thereof, or the like.

As used herein, the term "actuator" refers to any structure that can be used to move the medical device between a deployed and non deployed orientation. For instance, an actuator can be used to pull or push on a tube having a number of openings or slits to open or close the device. The actuator can optionally be at a central location, internal to the device, but might also be located as an intermediate or outer layer of the device. The actuator can be made from a tube, wire, coiled (or other shape) spring, stent-like spring, or other shapes. A pull-only actuator can be formed from a (braided) cable, string-like element, or similar. An actuator tube outside a center slit tube might include 'windows' through which the slit tube can deploy if moving in the outward direction. Generally, the "actuator" can have all or portions thereof fabricated from one or more metals, alloys, polymers, plastics, synthetic materials, shape memory materials, including shape memory alloys and/or shape memory plastics, combinations thereof, or the like.

As used herein the term "slit" refers to a long or short, narrow or wide, opening in a structure. For instance, any opening through the wall of the tube can be described as a "slit". These slits can leave any shape in the wall such as long or short elements, or other shapes such as spiral, mesh-like, or others as may be desired to obtain the functions or performance desired.

As used herein, the term "slit member" refers to any elongate structure, optionally having a lumen that extends from one end towards another end, and has one or more slits. The "slit member" can be fabricated by various techniques, and optionally can include tubular members, wires, strips of metal or other material, mesh, etc.

Figure 8:
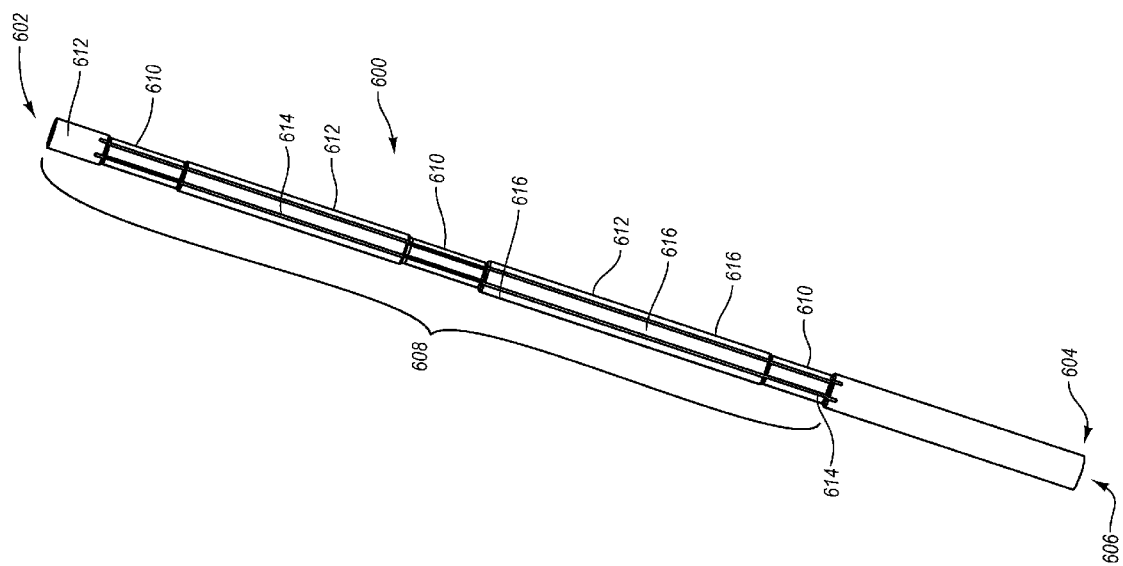
FIG. 8 is a perspective view illustrating an embodiment of a medical device in a non deployed orientation.

Turning to FIG. 8, illustrated is a perspective view of one configuration of a medical device 600 that can be used as an anchor to close a PFO. As illustrated, the device 600 has a body member or element having a distal end 602, a proximal end 604, and a lumen 606 extending from the distal end 602 towards the proximal end 604. Although the proximal end 604 is shown in close proximity to the distal end 602, it will be understood that the proximal end 604 can be distant from the distal end 602, such as outside the patient's body, etc. It will also be understood that the lumen 606 can terminate distal to the proximal end 604 or can terminate at the proximal end 604. As such, the medical device 600 can be configured for use in over-the-wire and/or rapid exchange environment. Further, the medical device 600 can be modified to accommodate a monorail type configuration.

As illustrated, the body member of the medical device 600 can have variable wall thickness along its length from the distal end 602 towards the proximal end 604. It will be understood that in some configurations, a distal portion 608 can have a variable wall thickness while the remainder of the body member of the medical device 600 toward the proximal end 606 has a generally uniform cross-section. It will also be true that other configurations of the medical device 600 will have different combinations of wall thicknesses.

With continued reference to FIG. 8, the distal portion 608 can include thin-walled sections 610 and wall sections 612 having a wall thickness greater than the thin-walled sections 610. In the illustrated embodiment, a plurality of slits 614 extend along at least a portion of the distal portion 608. These slits 614 cause the distal portion 608 to be separated into a number of struts or legs 616 and cause the medical device 600 to have a slit tube configuration.

Figure 9:
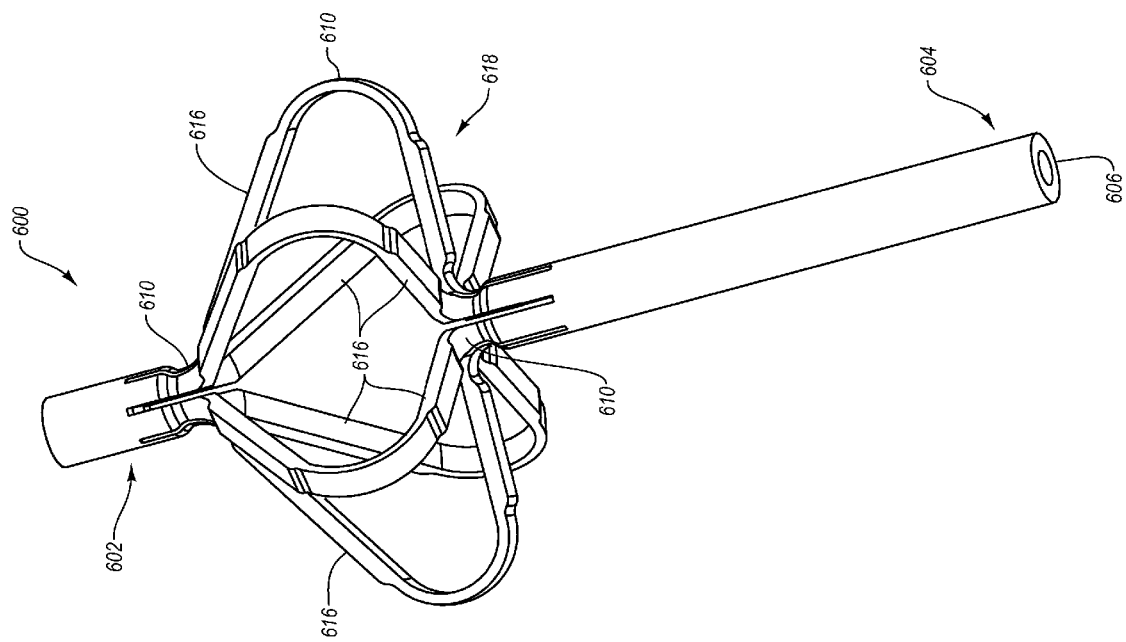
FIG. 9 is a perspective view illustrating the medical device of FIG. 8 in a deployed orientation.

When the distal end 602 is moved toward the proximal end 606, or vice versa, such as under the influence of an actuator 620 (FIG. 11) or because at least a portion of the struts or legs 616 are biased to move outwardly, the slits 614 enable the struts or legs 616 to move and create the configuration illustrated in FIG. 9. Stated another way, the combination of struts or legs 616 and slits 614 results in the distal portion 608 creating an anchor 618 upon moving the distal end 602 toward the proximal end 606, or vice versa. Although six struts or legs 616 and slits 614 are illustrated, it will be understood that a lesser or greater number or struts or legs 616 and slits 614 can be used.

With continued reference to FIG. 8, the distal portion 608 can be considered a deployment section of the medical device 600. When in a deployed orientation as illustrated in FIG. 9 this portion or section functions as the anchor 618 or other structure used to move portions of the septum secundum and/or septum primum during a procedure to close a PFO. For instance, when the medical device 600 is passed along path 99 (FIG. 1) through the PFO to the left atrium 40, whether or not with the use of a separate catheter (not shown), the distal portion 608 can be deployed to form the anchor 618. The struts or legs 616 can contact the septum secundum and/or septum primum to close the PFO in preparation for application of RF energy, as will be discussed in more detail hereinafter.

Returning to FIG. 8, although there are three thin-wall sections 610 illustrated, it will be understood that there can be more or less than three as is desired. The use of wall sections 610 and 612 provides flexibility to distal portion 108. More specifically, the thinner, more flexible sections 610 can act as flexible elements (hinges or pivots) while sections 612 that are thicker and/or stiffer can remain, in one configuration, straighter, giving a particular shape to the deployed anchor. The ratios of the lengths of sections 612 (the thicker and stiffer sections) to sections 610 can serve to define the deployed shape. Further, the combination of sections 610 and 612 enables the distal portion 608 to expand outwardly as the distal end 602 is moved toward the proximal end 606, or vice versa. The particular location of the sections 610 defines the location where the distal portion 608 expands outwardly and/or inwardly, as will be discussed in more detail hereinafter.

The use of the term "thin-wall" merely refers to a portion of the medical device 600 that has a wall thickness less than another portion of the medical device 600, such as wall sections 612 and/or the portion of the medical device 600 extending from the distal portion 608 towards the proximal end 604.

Although the medical device 600 is illustrated as having only a single deployment section or anchor 618, one skilled in the art will appreciate that other medical devices can include single, double (see FIG. 10), or multiple deployment sections or anchors 618 as desired.

The medical device 600 can be used with the struts or legs 616 biased to be in either a closed configuration or non deployed orientation (see FIG. 8) or an open position or deployed orientation (see FIG. 9). Depending upon the particular configuration, deployment of the medical device 600 can occur in a variety of different manners. For either case, however, the medical device 600 can be first positioned in either the right atrium 30 or the left atrium 40. This can be accomplished, in one configuration, by positioning a catheter in either the right atrium 30 or the left atrium 40 and then passing the medical device 600 through the catheter. Alternatively, the medical device 600 can function as a guide wire, with associated torqueability, flexibility, etc, including the inclusion of a J-tip or other flexible tip extending from the distal end 602, and steered into the right atrium 30 or the left atrium 40. Further, the medical device 600 can be mounted to the end of the actuator 620 (FIG. 11), with the combination of medical device 600 and actuator 620 (FIG. 11) functioning as a guide wire.

With reference to the first scenario, i.e., use of a catheter, once positioned, it is possible to deploy the medical device 600 from within the catheter by pushing at least the distal portion 608 of the medical device 600 out of the catheter (not shown), moving the catheter proximally to the distal portion 608 of the medical device 600, or a combination thereof. This can be achieved by way of the actuator 620 (FIG. 11), which can be releasably (such as by a threaded connection, interference connection, etc) or permanently attached to either the distal end 602 or the proximal end 604 of the medical device 600. Alternatively, such as when the proximal end 604 is distant from the distal end 602, i.e., the proximal end 604 is outside the patient's body, moving the proximal end 604 in the desired direction can deploy the distal portion 608 from within the catheter.

When the struts or legs 616 are biased to open, i.e., the configuration of FIG. 9, moving the distal portion 608 outside the catheter results in the struts or legs 616 moving to the biased configuration. Alternatively, when the struts or legs 616 are biased to the closed configuration, i.e., FIG. 8, moving the actuator 620 or a secondary actuator (not shown) proximally following deployment of the distal portion 608 outside the catheter results in the struts or legs 616 moving to open configuration illustrated in FIG. 9.

Turning now to the second scenario, i.e., without a catheter, once the medical device 600 has the positioned into the right atrium 30 (FIG. 1A) or the left atrium 40 (FIG. 1A), the actuator 620 or a secondary actuator associated with the actuator 620 (such as within a lumen of the actuator or in close proximity to the actuator) can be moved in a proximal direction to move the distal end 602 towards the proximal end 604.

Optionally, the proximal end 604 can be moved distally as the actuator 620 moves proximally. Alternatively, the proximal end 604 can be moved distally while the actuator 620 is maintained in a fixed position. No matter the particular movement of the distal end 602, the proximal end 606 or the actuator 620 (or the secondary actuator), the struts or legs 616 move in accordance with the particular location of the sections 610 to create the anchor configuration depicted in FIGS. 11 and 12.

Figure 11:
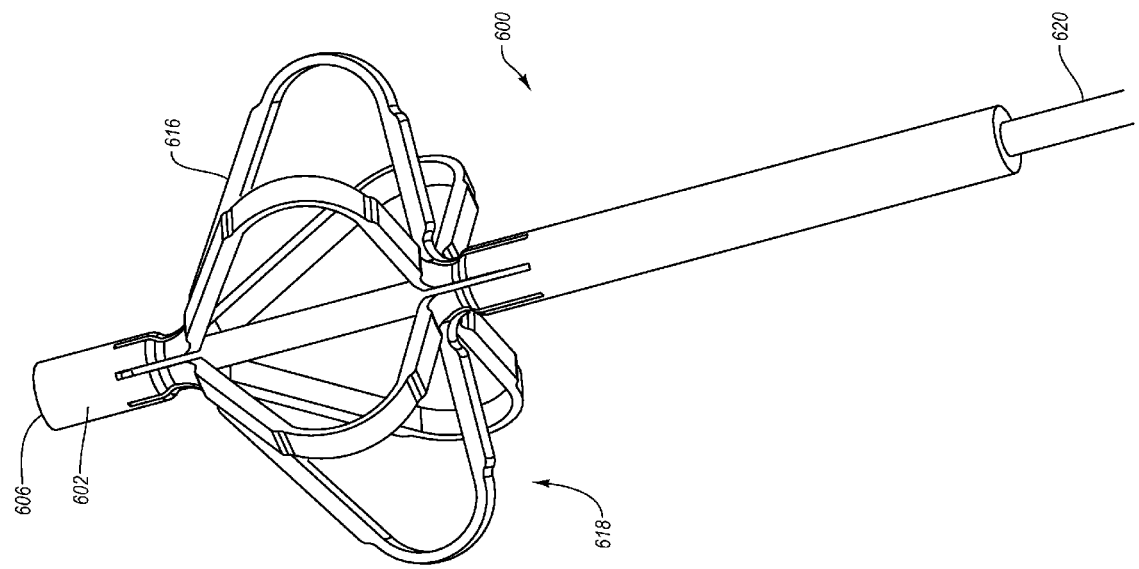
FIG. 11 is a perspective view illustrating an embodiment of a medical device including an actuator.
Figure 12:
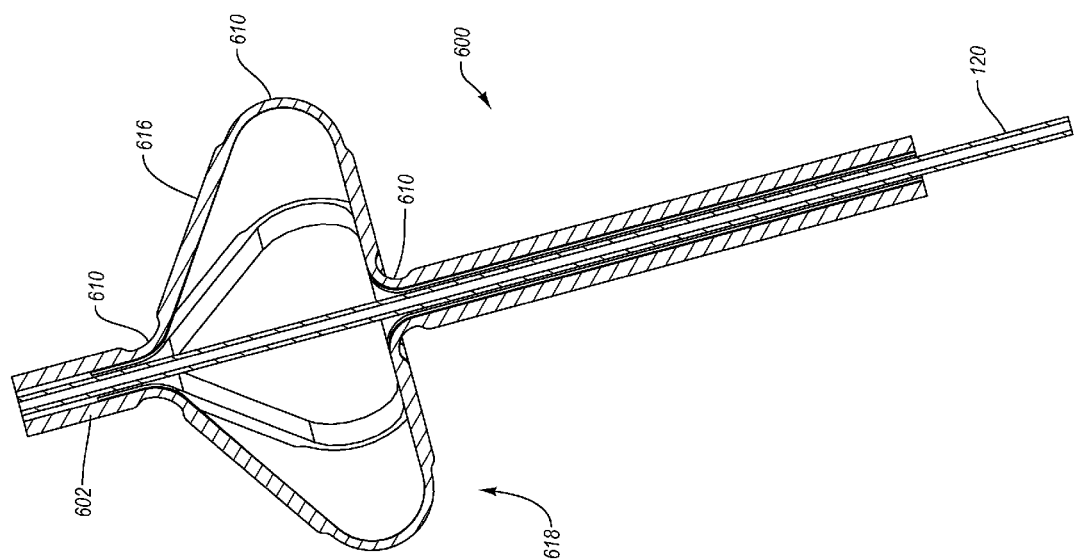
FIG. 12 is a cross-sectional view illustrating the medical device of FIG. 11.

It will be understood that in another configuration, such as when the struts or legs 616 are biased to the expanded or open configuration, i.e., the anchor configuration of FIGS. 11 and 12, the distal portion 608 can be restrained by a restraining member or structure (not shown). This restraining member can prevent the distal portion 608 from transitioning between the deployed and non deployed orientation until the restraining member or structure is released. Various structures can be used to form such restraining member, such as but not limited to releasable sleeves, films, wires, or the like. Further, the restraining member can have the form of a sleeve that can slide relative to the medical device 600 and so release the distal portion 608. One skilled in the art can identify various other configurations of the restraining member.

Figure 10:
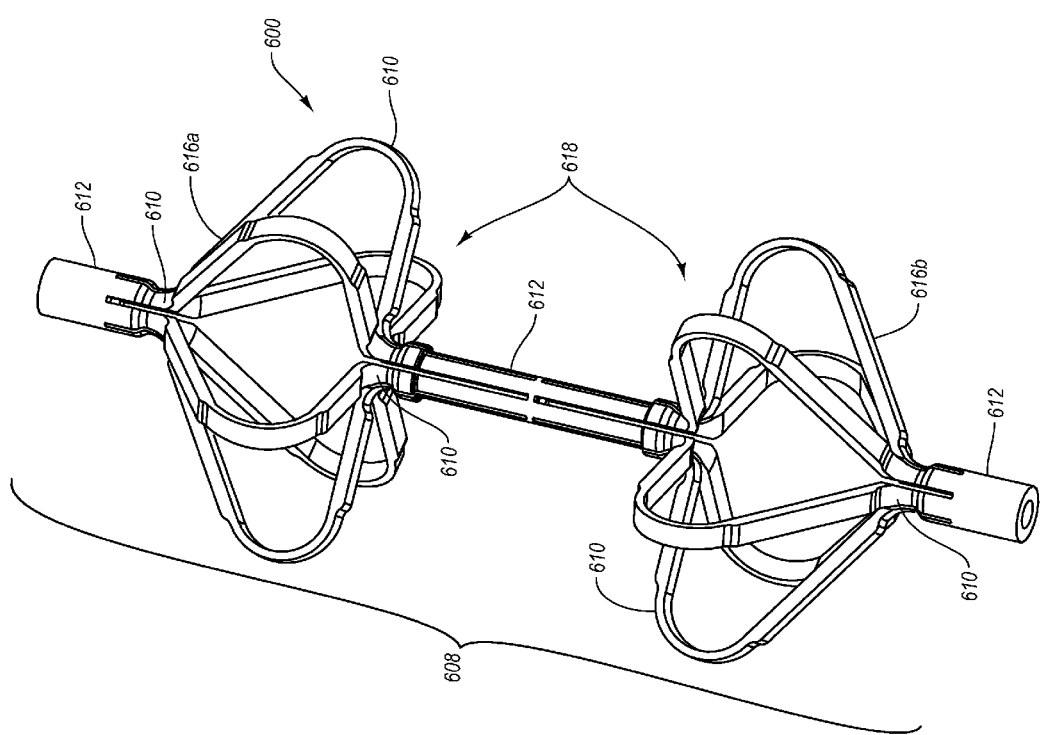
FIG. 10 is a perspective view illustrating an embodiment of a medical device.

For a multi-section medical device, such as that illustrated in FIG. 10, the above-described method of deploying the medical device is also applicable. In the case of multiple sections, the strength of each section can be tailored to cause each section of the device to open in a desired sequence (e.g.—distal first, proximal next after addition of more force to deploy the medical device). Further, it may be desirable to have multiple sections of the device that open when the actuator is operated. By so doing, an anchor can be positioned on both sides of a PFO across the atrial septum. In addition, in the case of multiple sections, the strength of each section can be tailored to cause each section of the device to open in a desired sequence (e.g.—distal first, proximal next after addition of more actuator force). Furthermore, if the sections are biased in a deployed orientation, then movement of the medical device 600 through a catheter (not shown), for example, will cause the first exposed section to deploy and then upon exposure of the subsequent section from the catheter will cause the subsequent section to deploy.

More generally, the use of actuator 620 provides control over delivery of the medical device to the left or right atrium. As mentioned above, the actuator 620 and/or another actuator member, attached at one end of the slit tube, can be used to compress the medical device 600 axially (against a restraining element, such as the catheter or another separate structure the restrains the struts or legs 616 in a closed configuration) and thus cause it to expand (or collapse depending on configuration) radially, thus opening or deploying the anchor.

The medical devices illustrated in FIGS. 8-10 can be fabricated from a variety of different materials. In one configuration, the medical device can be at least partially fabricated from a shape memory material, such as a shape memory alloy or a shape memory plastic. By using the shape memory material the medical device can be trained during manufacture in an expanded configuration such that deployment of the medical device from a catheter into the right atrium 30 or left atrium 40 causes the struts or legs 616 will extend outwardly. For instance, the medical device 600 can be constrained in the closed configuration of FIG. 8 by way of a catheter or other structure or system to maintain the struts or legs 616 in a closed configuration during insertion into the right atrium 30 and/or left atrium 40. Once positioned, the catheter can be withdrawn or the medical device pushed out of the catheter or other structure that restrains the struts or legs 616 using an actuator to allow the struts or legs 616 to open. Pulling the medical device back into the catheter or other structure through use of the actuator would close the struts or legs 616.

Figure 1B:
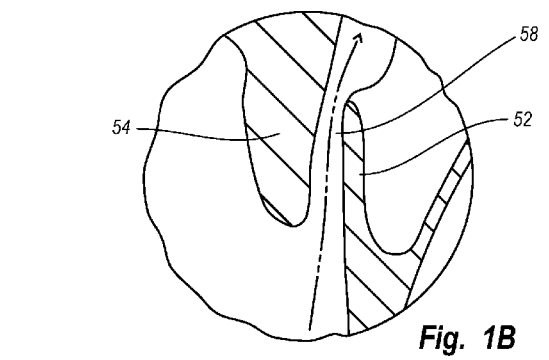
FIG. 1B is an enlarged cross-section view illustrating the septum primum and the septum secundum and a PFO tunnel between the septum primum and the septum secundum.
Figure 1C:
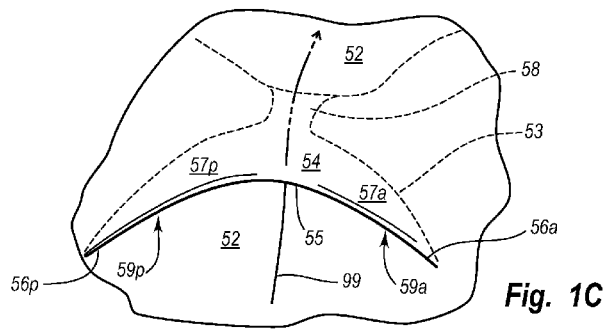
FIG. 1C is a perspective view illustrating the septum secundum with the tunnel and the septum primum shown in phantom.

As discussed above with respect to FIG. 10, the medical device or anchor of the present invention can include one or more deployment sections or anchors. These deployment sections or anchors can be used to close a PFO as one deployment section or anchor is located in the left atrium (FIG. 1A) and another deployment section or anchor is located in the right atrium (FIG. 1A). A medical device having two deployment sections or anchors can be identified as a "double-ended" or "double-anchored" medical device because it includes two deployment sections or two anchors.

Figure 13:
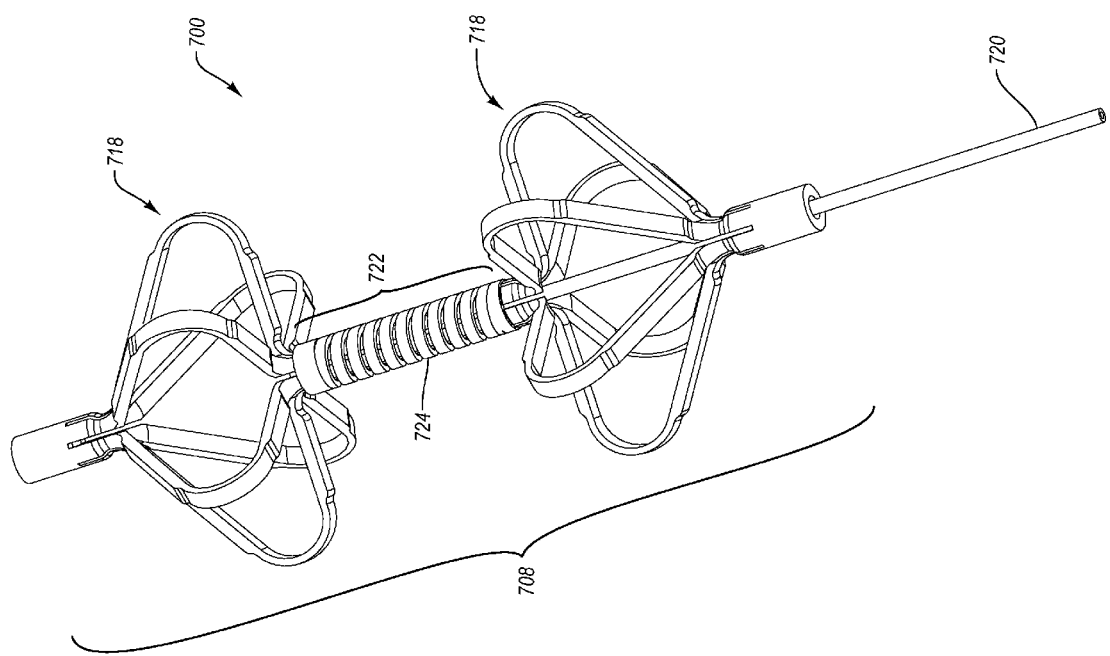
FIG. 13 is a perspective view illustrating an embodiment of a medical device including a flexing member.
Figure 14:
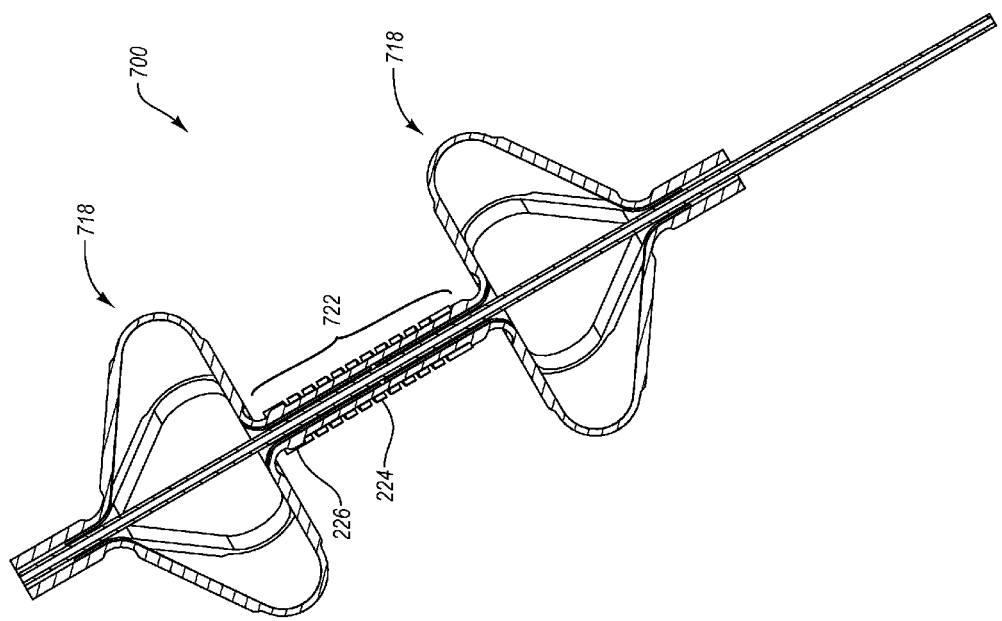
FIG. 14 is a cross-sectional view illustrating the medical device of FIG. 13.

Turning to FIGS. 13 and 14, illustrated is one example of a double-ended or double-anchored medical device, identified by reference numeral 700, which can be used to close the opposite sides of a PFO against themselves. In particular, the medical device 700 has the ability for each side of the medical device 700 to flex or rotate relative to the other, with or without the actuator 720 attached thereto. Stated another way, the medical device 700 can include two anchors 718 that can move relative to one another, such as the anchors 718 relative position one to another can vary during implanting and/or use. In particular, an intermediate portion 722 of the medical device 700, whether alone or in combination with the remainder of the medical device 700, such as the anchors 718 and the actuator 720, enables flexing and/or rotational motion of one of the anchors 718 relative to the intermediate portion 722 and/or the other respective anchor 718. By enabling the movement, increased PFO closure efficiency can be obtained. In addition, varying the relative position of the different portions of the medical device 700 can facilitate proper closure of the opening.

With continued reference to FIGS. 13 and 14, the intermediate portion 722 can have a similar configuration to distal portion 708 of the medical device 700. For instance, the walls of the "slit tube" forming the medical device 700 can be thinned at the intermediate portion 722 to enable the medical device 700 to flex as desired. In addition thinning the walls at the thinned portion 726 of the intermediate portion 722, an optional flexing member 724 can be wrapped around the thinned portion 726 to restrain the struts or legs formed in the slit tube and prevent undesirable movement, i.e., unwanted movement in undesired directions. For instance, the flexing member 724 can prevent the struts or legs from opening radially when only bending or twisting along the length of the device is desired. The flexing member 724 can have various configurations, such as a coil, strip, or tubular member, and be fabricated of one or more metals, alloys, polymers, plastics, synthetic materials, shape memory materials, including shape memory alloys and/or shape memory plastics, combinations thereof, or the like.

Figure 15:
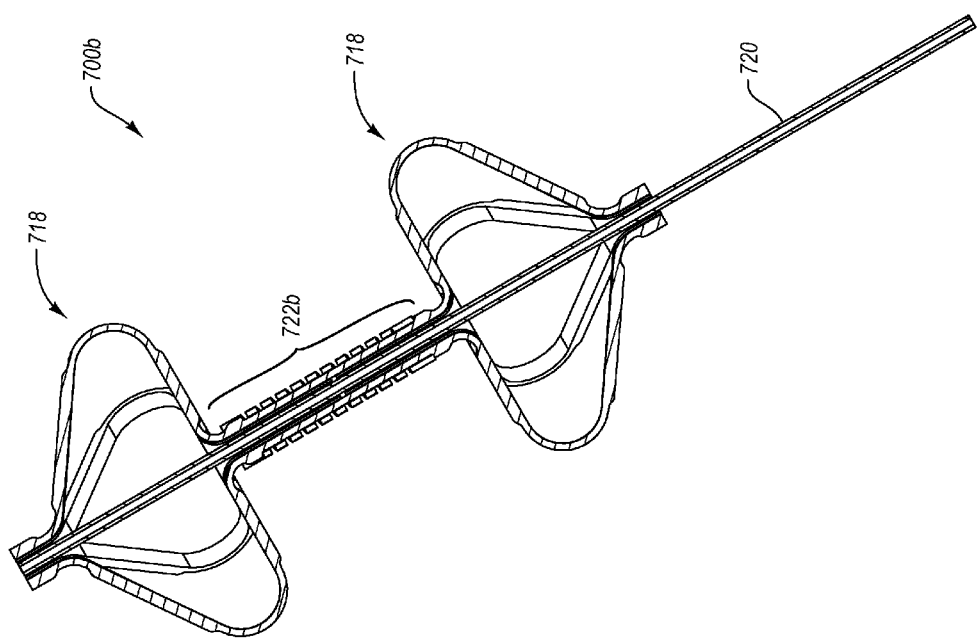
FIG. 15 is a cross-sectional view illustrating an embodiment of a medical device including a flexing member.

In an alternative configuration to the above, identified as medical device 700b in FIG. 15, the functionality of the flexing member 724 (FIG. 14) can be incorporated in the "slit tube" forming part of the intermediate portion 722b. For instance, and not by way of limitation, a spiral cut in the walls of the "slit tube" can create a coil spring shape that is stiff axially, but soft in lateral bending and/or rotation. It would be understood that the particular cuts used to make the "split tube" of the intermediate portion 722b capable of flexing need not be spiral but can be transverse, diagonal, or parallel to the longitudinal axis of the intermediate portion 722b. Further, combinations of any of the above-described cuts can be used on the intermediate portion 722b.

It will be understood that the actuator 720 in FIGS. 13-15 can also be configured to flex with the intermediate portion 722, 722b. This can be achieved using similar techniques to those to make the intermediate portion 722, 722b to flex. In addition, the materials forming the actuator 720 can be selected so that at least a portion of the actuator 720 can flex. For instance, the portion of the actuator 720 corresponding to the intermediate portion 722, 722b can be configured to flex as the intermediate portion 722, 722b flexes, while the remainder of the actuator 720 flexes less than such portion.

In still another configuration, the double-ended or double-anchored medical device can include two spaced apart anchors that are connected together by way of a separate flexible member. For instance, and with reference to FIG. 15, the intermediate portion 722b can be a separate flexible section, such as a coil spring, wire, or other flexible member connected or mounted to two anchors, instead of being formed by cutting the "slit tube" forming the medical device 700b. In this manner, the degree of allowable flexibility of the intermediate portion can be varied without varying the construction of the anchors. This enables numbers different medical devices to be manufactured while maintaining substantially similar anchors.

As with the flexing member 724 of FIG. 14, the flexible section can have various configurations, such as a coil, strip, or tubular member, and be fabricated of one or more metals, alloys, polymers, plastics, synthetic materials, shape memory materials, including shape memory alloys and/or shape memory plastics, combinations thereof, or the like.

Generally, the different portions of the double-ended or double-anchored medical device, such as the anchors, the struts or legs, the intermediate portion, etc can be configured with various strengths and stiffnesses to provide certain functionality. For instance, and not by way of limitation, the materials and configuration of the medical device can be chosen so that the distal anchor can open first, such as in the left atrium, the proximal anchor opens following the distal anchor, such as in the right atrium, and the intermediate portion or a flexure element in between the two anchors contracts lastly, thus capturing the PFO and septum between the two open anchors as the actuator is moved, such as in the proximal direction.

Figure 16:
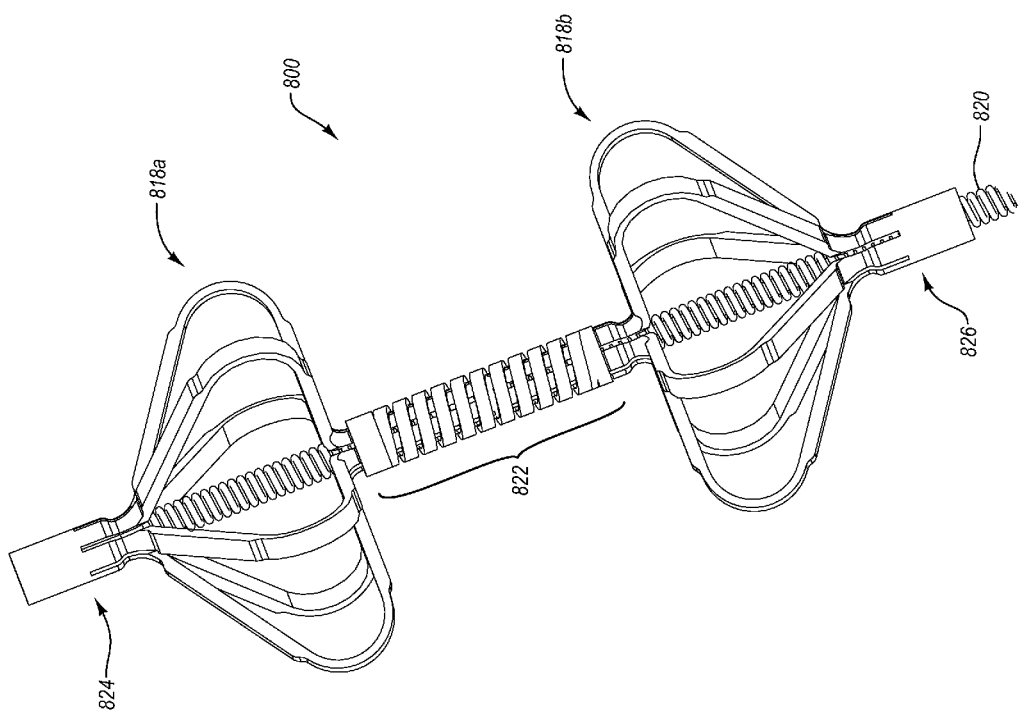
FIG. 16 is a perspective view illustrating an embodiment of a medical device having a flexible actuator.
Figure 17:
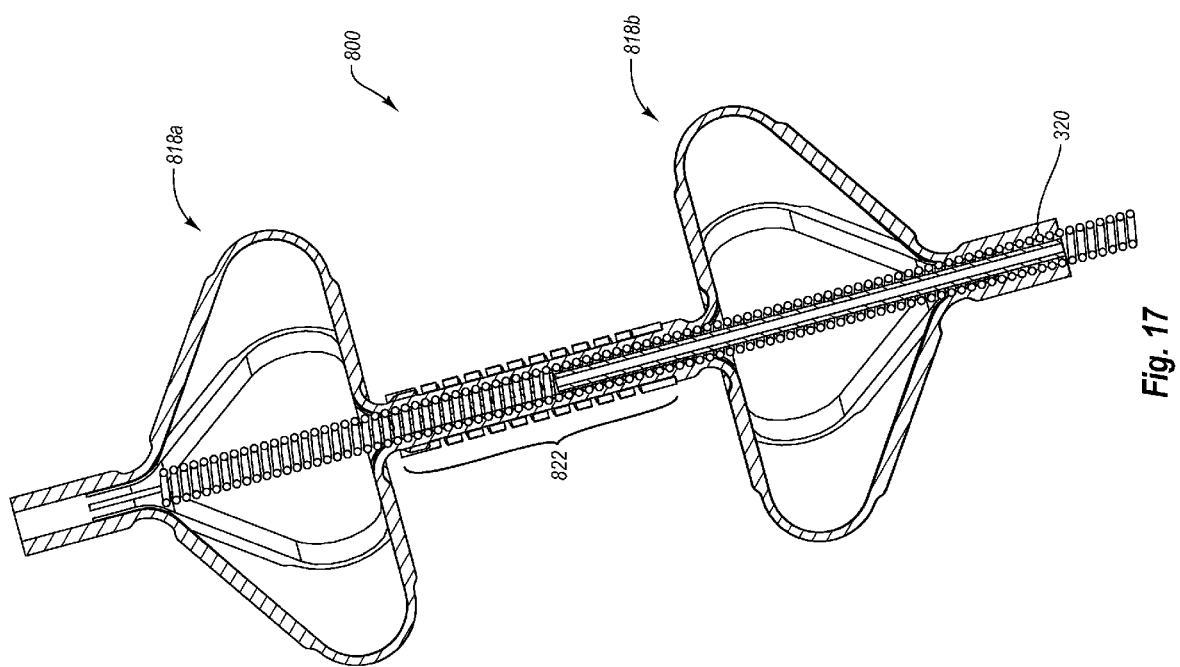
FIG. 17 is a cross-sectional view illustrating the medical device of FIG. 16.

Turning now to FIGS. 16 and 17, illustrated is another medical device 800 that can function in a similar manner to the other medical devices described herein. As such, the teaching and discussion with respect to the other described medical devices also apply to the medical device 800. As such, like elements will be designated with like reference numerals.

As shown in FIG. 16, the medical device 800 has a double-ended or double-anchored configuration. A first anchor 818a is separated from a second anchor 818b by an intermediate portion 822. The intermediate portion 822 can flex and can be similar to the intermediate portion 822 or 822b. Extending from a distal end 824 towards and past a proximal end 826 of the medical device 800 is an actuator 820. Actuator 820 can have a similar configuration to actuator 620 and 720 described herein. For instance, actuator 820 can be a generally solid member that can flex to some degree. In the illustrated configuration, actuator 820 is configured to flex at least to the degree that the generally solid member flexes, and based upon the illustrated configuration, the actuator 820 can flex more than actuators 620 and 720. Increased flexibility or force limitation can be achieved by forming the actuator 820 from a coil or spring. Alternatively, the actuator can be a hypo-tube or solid member having one or more cuts that increase its flexibility. More generally, the actuator can be any structure that functions as the actuator, i.e., optionally aid with deploying the anchors and/or moving the anchors relative to one another during PFO closure.

The actuator 820 can be fabricated of one or more metals, alloys, polymers, plastics, synthetic materials, shape memory materials, including shape memory alloys and/or shape memory plastics, combinations thereof, or the like.

FIG. 17 illustrates a cross-sectional view of medical device 800.

Figure 18:
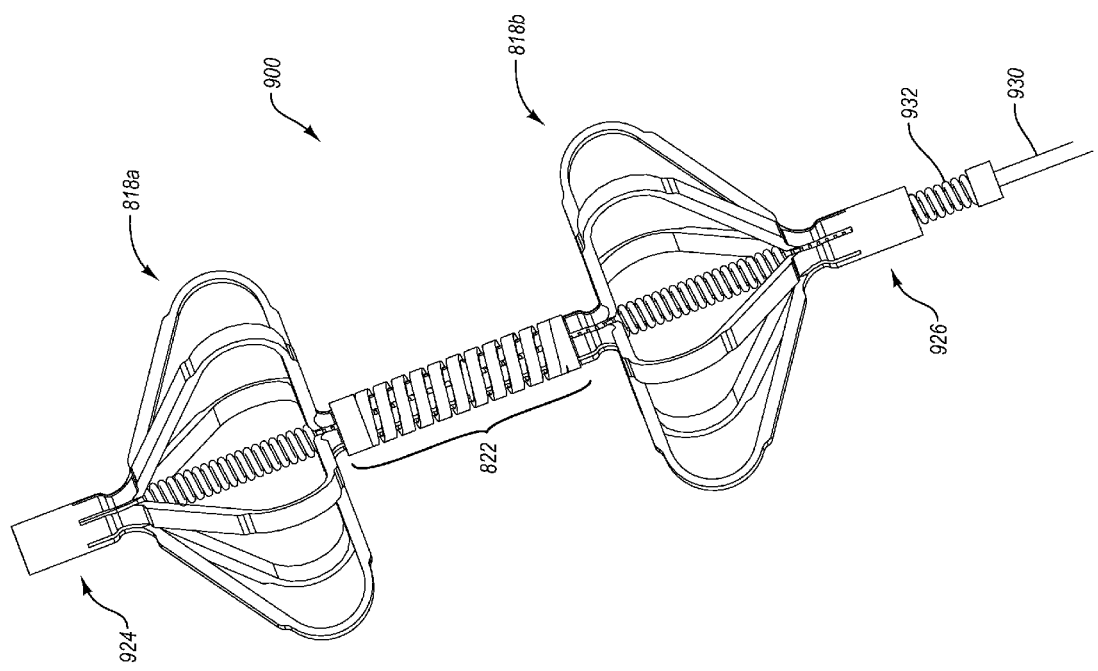
FIG. 18 is a perspective view illustrating an embodiment of a medical device including an actuator member and a cable guide.

With reference to FIG. 18, illustrated is another configuration of a medical device 900 having an actuator usable with the described medical devices. In the illustrated embodiment, the actuator includes a cable guide 930 and an actuator member 932. The actuator member 932 can have a similar configuration to the actuator 820, but terminates at a location just proximal to the proximal end 926 of the medical device 900. Stated another way, the actuator member 932 extends from a distal end 924 towards the proximal end 926 of the medical device 900 and terminates at a location distal to the proximal end of the cable guide 930.

Extending at least partially through the actuator member 932 is the cable guide 930. The cable guide 930 minimizes the effect of actuator tension on the angulation of the distal anchor 818a when deployed. The cable guide 930 can be fabricated of one or more metals, alloys, polymers, plastics, synthetic materials, shape memory materials, including shape memory alloys and/or shape memory plastics, combinations thereof, or the like.

Each of the medical devices described herein can optionally function as RF electrodes, whether monopolar or bio-polar electrodes. As such, at least a portion of the medical device can be conductive so that RF energy can be applied to the tissue in and/or around the PFO to close the PFO. It will be understood that the medical devices disclosed herein can be electrically connected to an RF energy source outside a patient's body and receive such RF energy to tissue weld the PFO closed. In one configuration, the actuator can be electrically conductive and be used to deliver RF energy to the medical device, including the deployment section. Alternatively, separate electrical connections, traces, wires, or the like can be associated with different portions of the medical device to enable RF energy delivery to the tissue in and/or about the PFO.

Furthermore, it will be understood that various devices, such as those described and designated by reference 120 as illustrated in FIGS. 2 and 3, can be used in connection with the medical devices. For example, impedance electrodes, RF electrodes and/or temperature measuring devices can be used in connection with the medical devices described with respect to FIGS. 8-18 without departing from the scope and spirit of the invention. Likewise, it will be understood that such devices can be located on the medical devices in various locations. For example, one or more devices, such as a thermocouple, RF electrode and/or impedance electrode, can be coupled to any and/or all of the following: thin-walled section 110, walled section 112, distal end 102 or other locations on the medical device in order to deliver RF energy to, and/or facilitate measurement of various characteristics of, the tissue adjacent the PFO. In this manner, RF doses and be determined and applied utilizing the medical devices disclosed herein.

It will be understood by one of ordinary skill in the art in view of the disclosure provided herein that the devices and methods described herein can use or be used with any of the anchors, electrodes or structures of medical devices described in various related patent applications, including U.S. patent application Ser. No. 10/964,311, filed Oct. 12, 2004, U.S. patent application Ser. No. 11/102,095, filed Apr. 8, 2005, U.S. patent application Ser. No. 11/534,996, filed Sep. 25, 2006, and U.S. patent application Ser. No. 11/534,953, filed Sep. 25, 2006.

In one embodiment, a medical device usable to close a PFO can include an elongate body member having a lumen extending from a distal end towards a proximal end, the body member having a plurality of first struts defining a first anchor, said first struts being biased in a closed configuration, and an actuator extending from said distal end towards said proximal end through said lumen, said actuator movable to move said distal end towards said proximal end to move said biased plurality of first struts from said closed configuration to an open configuration. This medical device can also include a plurality of second struts formed in said body member and defining a second anchor, said plurality of second struts being biased in either a closed or open configuration. Furthermore, said actuator can pass through said second anchor.

In another embodiment, a closure device for determining RF dose for closing a PFO includes a left closure device comprised of arms having a shape memory material, the arms having been preformed to have a predetermined curved shape and having at least one impedance electrode in electronic communication with an electronic controller, the arms being capable of being restrained within a left atrial delivery shaft in a relatively straight position for delivery into a patient, and being capable of assuming their predetermined shape upon being deployed from the left atrial delivery shaft, and upon being deployed into a left atrium of a patient and thereby becoming unrestrained from the left atrial delivery shaft, the arms assume their predetermined curved shape, wherein the predetermined curved shape is configured such that applying a retracting force to the arms with respect to the left atrial delivery shaft will retract the arms into the left atrial delivery shaft, and said retracting the arms and left atrial delivery shaft with respect to a tissue defining the PFO opening causes the arms to flatten against the tissue to maximize the contact area between the arms and the tissue and to force the tissue defining the PFO opening to contact so as to close the PFO. This closure device can also include a left atrial delivery tube in electronic communication with the at least one impedance electrode such that current is capable of being communicated between the at least one impedance electrode and the controller, and on an inner surface with the left atrial delivery shaft and having electrical insulation on a outer surface, and a right electrode catheter encompassing the left atrial delivery tube, the right electrode catheter being in communication with one or more right electrodes such that current can be applied across tissue separating the left electrode and the right electrode measures impedance of the tissue.

In another embodiment, a closure device for closing a PFO with RF energy includes a right closure device comprised of arms having a super-elastic, for example, shape memory material, the arms having been preformed to have a predetermined curved shape and having at least one RF electrode in electronic communication with an electronic controller, the arms being capable of being restrained within a right atrial delivery shaft in a relatively straight position for delivery into a patient, and being capable of assuming their predetermined shape upon being deployed from the right atrial delivery shaft, and upon being deployed into a right atrium of a patient and thereby becoming unrestrained from the right atrial delivery shaft, the arms assume their predetermined curved shape, wherein the predetermined curved shape is configured such that applying a retractile force to the arms with respect to the right atrial delivery shaft will retract the arms into the right atrial delivery shaft, and pushing deployed arms and right atrial delivery shaft with respect to a tissue defining the PFO opening causes the arms to flatten against the tissue to maximize the contact area between the arms and the tissue and to force the tissue defining the PFO opening to contact so as to close the PFO. This closure device can also include a right atrial delivery tube in electronic communication with the at least one RF electrode such that current is capable of being communicated between the at least one RF electrode and the controller, and on an inner surface with the right atrial delivery shaft and having electrical insulation on a outer surface, and a guide wire extending from a lumen in the right atrial delivery tube and being configured to guide the right closure device to the tissue.

The present invention may be embodied in other specific forms without departing from its spirit or essential characteristics. The described embodiments are to be considered in all respects only as illustrative and not restrictive. Exemplary claims have been included herein to illustrate embodiments of the invention. Although exemplary claims are presented, the invention is not limited to these claims, and the applicant reserves the right to present different or other claims in the future in view of the embodiments of the invention described herein.

What is claimed is:

1. A medical system for use in reducing the size of an internal tissue opening comprising:
   a delivery sheath having a distal end and a proximal end, wherein said delivery sheath includes a lumen defining an axis extending from said proximal end toward said distal end;
   an electrode including one or more arms, said one or more arms being configured to be extended from said distal end of said delivery sheath to be received through an internal tissue opening, said electrode being configured to delivery radio frequency energy to tissue which is in contact with at least one of said one or more arms;
   a first device being positioned proximate to at least one of said arms; and
   a second device, wherein when said electrode is positioned against a first side of the internal tissue opening and said second device is positioned proximate a second opposing side of the internal tissue opening, said first and second devices usable to measure a tissue characteristic enabling a practitioner to determine a radio frequency dose for use in reducing the size of the internal tissue opening,
   wherein said delivery sheath includes a second lumen, the second lumen being non-concentric relative to the axis defined in the lumen of the delivery sheath, wherein said second device is positioned within said second lumen and is capable of movement independent of said electrode and said delivery sheath.

2. The medical device of claim 1, further comprising a second electrode configured to be positionable proximate the second side of the internal tissue opening.

3. The medical device of claim 1, wherein said first device comprises a first thermocouple and said second device comprises a second thermocouple.

4. The medical device of claim 2, wherein said first device is coupled to one of said one or more arms of said first electrode and a third device is coupled to said second electrode.

5. The medical device of claim 3, wherein said first thermocouple measures the temperature of the tissue on the first side of the internal tissue opening and said second thermocouple measures the temperature of the tissue on the second side of the internal tissue opening.

6. The medical device of claim 4, wherein said first device comprises a first impedance electrode and said third device comprises a second impedance electrode.

7. The medical device of claim 6, wherein said first and second impedance electrodes measure the impedance of the tissue between the first and second sides of the internal tissue opening to facilitate the determination of an radio frequency dosage to treat the internal tissue opening.

8. The medical device of claim 4, wherein said first device comprises either an impedance electrode, a radio frequency electrode or a thermocouple, and wherein said second device comprises either an impedance electrode, a radio frequency electrode or a thermocouple.

* * * * *